United States Patent [19]

Singh et al.

[11] Patent Number: 5,420,334
[45] Date of Patent: May 30, 1995

[54] INHIBITORS OF FARNESYL-PROTEIN TRANSFERASE

[75] Inventors: Sheo B. Singh, Edison; Gerald F. Bills, Clark; Russell B. Lingham, Watchung, all of N.J.; Isabel Martin, Madrid, Spain; Keith C. Silverman, Somerset; Jack L. Smith, Colonia, both of N.J.

[73] Assignee: Merck & Co., Inc., Rahway, N.J.

[21] Appl. No.: 222,773

[22] Filed: Apr. 4, 1994

[51] Int. Cl.⁶ .............. A61K 31/66; A61K 31/12; A61K 31/22; A61K 31/44
[52] U.S. Cl. .............. 560/138; 560/179; 560/183
[58] Field of Search .............. 560/138, 179, 183; 514/510, 715, 717, 718

[56] References Cited

U.S. PATENT DOCUMENTS

| | | | |
|---|---|---|---|
| 5,043,268 | 8/1991 | Stock | 435/15 |
| 5,141,851 | 8/1992 | Brown et al. | 435/15 |
| 5,238,922 | 8/1993 | Graham et al. | 514/18 |
| 5,245,061 | 9/1993 | Singh | 554/121 |
| 5,256,399 | 10/1993 | Sessler et al. | 424/9 |
| 5,260,465 | 11/1993 | Singh et al. | 554/134 |
| 5,260,479 | 11/1993 | Singh | 560/190 |
| 5,276,217 | 1/1994 | Tius | 568/821 |
| 5,294,627 | 3/1994 | Arison et al. | 514/338 |
| 5,326,773 | 7/1994 | de Solms et al. | 514/336 |
| 5,340,828 | 8/1994 | Graham et al. | 514/357 |
| 5,350,867 | 9/1994 | Singh | 554/121 |
| 5,352,705 | 10/1994 | Deana et al. | 514/630 |

FOREIGN PATENT DOCUMENTS

| | | |
|---|---|---|
| 0456180A1 | 11/1991 | European Pat. Off. |
| 0537007A1 | 4/1993 | European Pat. Off. |
| WO9405274-A1 | 3/1994 | Japan . |
| 91/16340 | 10/1991 | WIPO . |

OTHER PUBLICATIONS

Kohl, N. E. et al., "Protein farnesyltransferase inhibitors block the growth of ras-dependent tumors in nude mice", Proc. Natl. Acad. Sci. USA, vol. 91, pp. 9141-9145 (Feb. 1994).

Aldridge, D. C. et al., Metabolites of Nectria coccinea, (Mar. 1972), J. C. S. Perkin I, pp. 2136-2141.

Bos, J. L., ras Oncogenes in Human Cancer: A Review (Apr. 1989), Cancer Research, 49, pp. 4682-4689.

Carey, S. T. and Nair, M. S. R. Metabolites from Pyrenomycetes VIII. Identification of Three Metabolites from Nectria Lucida as Antibiotic Triprenyl Phenols, (1977), The Journal of Natural Products, 40, No. 6, pp. 519-642.

Ellestad, G. A. et al., Some New Terpenoid Metabolites From An Unidentified Fusarium Species, (Feb. 1969), Tetrahedron, 25, pp. 1323-1334.

Gibbs, J. B. et al., Selective Inhibition of Farnesyl-Protein Transferase Blocks Ras Processing in Vivo, (Sep. 1993), The Journal of Biol. Chemistry, 268, No. 11, pp. 7617-7620.

Gibbs, J. B., Ras C-Terminal Processing Enzymes-New Drug Targets?, (Jun. 1991), Cell, 65, 1-4, pp. 1-4.

Goldstein, J. S., et al. Journal of Biological Chemistry, vol. 266, No. 24, pp. 15575-15578 (Jul. 1991).

James, G. L. et al., Benzodiazepine Peptidomimetics: Potent Inhibitors of Ras Farnesylation in Animal Cells, (Sep. 1993), Science, 260, pp. 1937-1942.

Kawagishi, H. et al., Isolation and Structure of a New Diprenyl Phenol, Colletorin B Produced by Cephalo- (List continued on next page.)

*Primary Examiner*—Arthur C. Prescott
*Attorney, Agent, or Firm*—David A. Muthard; Mark R. Daniel; Joseph F. DiPrima

[57] ABSTRACT

The present invention is directed to compounds which inhibit farnesyl-protein transferase (FPTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

20 Claims, No Drawings

OTHER PUBLICATIONS sporium diospyri, (Jul. 1984), Agric. Biol. Chem., 48 (7), pp. 1903–1904.

Kohl, N. E. et al., Selective Inhibition of ras–Dependent Transformation by a Farnesyltransferase Inhibitor, (Sep. 1993), Science, 260, pp. 1934–1937.

Leftheris, K. et al., Peptide Based P21RAS Farnesyl Transferase Inhibitors: Systematic Modification of the Tetrapeptide CA1A2X Motif, (Nov. 1994), Bioorganic & Medicinal Chemistry Letters, 4, No. 7, pp. 887–892.

Pompliano, D. L. et al., Steady-State Kinetic Mechanism of Ras Farnesyl:Protein Transferase, (Oct. 1992), Biochemistry, 31, pp. 3800–3807.

Qian, Y. et al., Design and Structural Requirements of Potent Peptidomimetic Inhibitors of p21ras Farnesyltransferase, (Nov. 1994), The Journal of Biological Chemistry, 269, No. 17, pp. 12410–12413.

Reiss, Y. et al., Inhibition of Purified p21ras Farnesyl:-Protein Transferase by Cys-AAX Tetrapeptides, (Aug. 1990), Cell, 62, pp. 81–88.

Reiss, Y. et al., Sequence requirement for peptide recognition by rat brain p21 ras protein farnesyltransferase, (Jun. 1991), Proc. Natl. Acad. Sci. USA, 88, pp. 732–736.

Sasaki, H. et al., Isolation and Structure of Ascochlorin and Its Analogs, (Feb. 1974), Agr. Biol. Chem., 38 (8), pp. 1463–1466.

Schaber, M. D. et al., Polyisoprenylation of Ras in Vitro by a Farnesyl-Protein Transferase, (Jan. 1990), The Journal of Biological Chemistry, 265, No. 25, pp. 14701–14704.

INHIBITORS OF FARNESYL-PROTEIN TRANSFERASE

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989)). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys—Aaa$^1$—Aaa$^2$—Xaa" box (Aaa is an aliphatic amino acid, the Xaa is any amino acid) (Willumsen et al., *Nature* 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a Cs terminal Cys farnesyl acceptor (Gutierrez et al., *EMBO J.* 8:1093–1098 (1989); Hancock et al., *Cell* 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys—Aaa$^1$—Aaa$^2$—Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634(1989)). Cytosollocalized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Recently, it has been demonstrated that certain inhibitors of farnesyl-protein transferase selectively block the processing of Ras oncoprotein intracellularly (N. E. Kohl et al. *Science*, 260:1934–1937 (1993) and G. L. James et al. *Science*, 260:1937–1942 (1993).

Previously, it has been demonstrated that tetrapeptides containing cysteine as an amino terminal residue with the CAAX sequence inhibit Ras farnesylation (Schaber et al., ibid; Reiss et. al., ibid; Reiss et al., PNAS, 88:732–736 (1991)). Such inhibitors may inhibit while serving as alternate substrates for the Ras farnesyl-transferase enzyme, or may be purely competitive inhibitors (U.S. Pat. No. 5,141,851, University of Texas).

Inhibitors of farnesyl protein transferase which are citraconic acid derivatives have been isolated as fermentation products from a strain of Chaetomella acutiseta (U.S. Pat. No. 5,260,465 and EP-54767 1-A). Synthetic analogs of those compounds have also been described (U.S. Pat. Nos. 5,245,061 and 5,260,479).

It is, therefore, an object of this invention to develop non-peptide compounds which will inhibit farnesyl-protein transferase and the farnesylation of the oncogene protein Ras. It is a further object of this invention to develop chemotherapeutic compositions containing the compounds of this invention, and methods for producing the compounds of this invention.

SUMMARY OF THE INVENTION

The present invention includes substituted phenol analogs which inhibit farnesyl-protein transferase and the farnesylation of the oncogene protein Ras, chemotherapeutic compositions containing the compounds of this invention, and methods for producing the compounds of this invention.

The compounds of this invention are illustrated by the following formula:

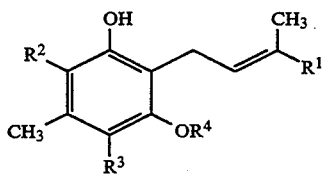

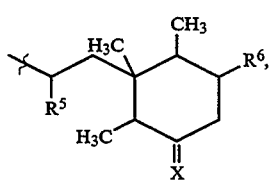

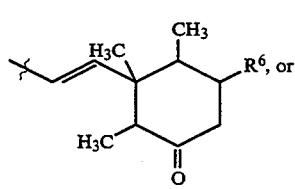

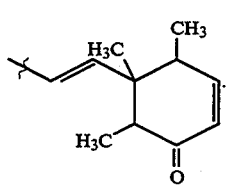

DETAILED DESCRIPTION OF THE INVENTION

The compounds of this invention are useful in the inhibition of farnesyl-protein transferase and, as a consequence, in the treatment of cancer. In a first embodiment of this invention, the inhibitors of farnesyl-protein transferase are illustrated by the formula I:

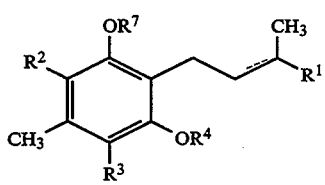

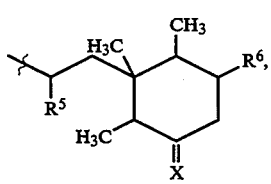

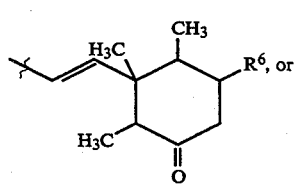

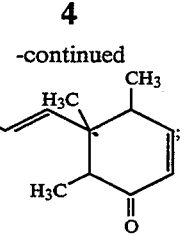

$R^2$ is hydrogen, formyl, $C_{1-4}$ alkyl, $-CO_2R^8$ or $-CH_2OH$;
$R^3$ is hydrogen or halogen;
$R^4$ is hydrogen, $C_{1-4}$ alkyl, $-CH_2OCH_3$, t-Bu(CH$_3$)$_2$Si— or acetyl;
$R^5$ is selected from:
  a) hydrogen; and
  b)

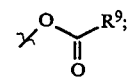

$R^6$ is hydrogen, $C_{1-4}$ alkyl or acetoxy;
$R^7$ is hydrogen, $-CH_2OCH_3$ or acyl;
$R^8$ is hydrogen or $C_1-C_6$ alkyl;
$R^9$ is $C_1-C_6$ alkyl;
the dashed line represents either a bond, thereby creating a double bond, or the absence of a second bond; and
X is O or —OH, H;
or the pharmaceutically acceptable salt thereof.

In a second embodiment of this invention, the inhibitors of farnesyl-protein transferase are compounds of the formula I:

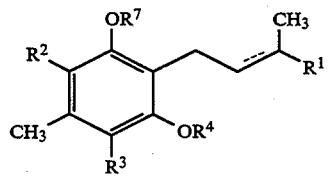

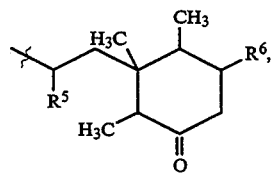

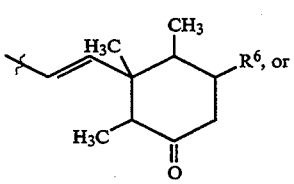

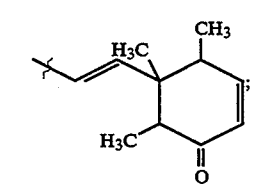

$R^2$ is hydrogen, formyl or $C_{1-4}$ alkyl;
$R^3$ is hydrogen or halogen;

$R^4$ is hydrogen, $C_{1-4}$ alkyl or acetyl;
$R^5$ is selected from:
 a) hydrogen; and
 b)

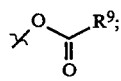

$R^6$ is hydrogen, $C_{1-4}$ alkyl or acetoxy;
$R^7$ is hydrogen or acyl;
$R^8$ is hydrogen or $C_1-C_6$ alkyl and
$R^9$ is $C_1-C_6$ alkyl;
or the pharmaceutically acceptable salt thereof.

In a third embodiment of this invention, the inhibitors of farnesyl-protein transferase are novel compounds of the formula I:

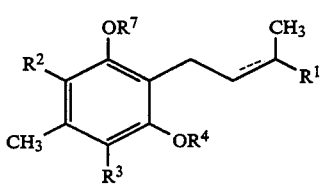   I wherein
$R^1$ is

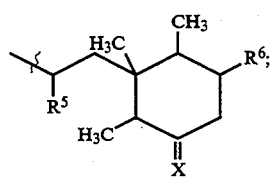

$R^2$ is hydrogen, formyl, $C_{1-4}$ alkyl, —$CO_2R^8$ or —$CH_2OH$;
$R^3$ is hydrogen or halogen;
$R^4$ is hydrogen, $C_{1-4}$ alkyl, —$CH_2OCH_3$, t-Bu($CH_3$)$_2$Si— or acetyl;
$R^5$ is selected from:
 a) hydrogen; and
 b)

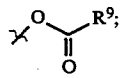

$R^6$ is hydrogen, $C_{1-4}$ alkyl or acetoxy;
$R^7$ is hydrogen, —$CH_2OCH_3$ or acyl;
$R^8$ is hydrogen or $C_1-C_6$ alkyl;
$R^9$ is $C_1-C_6$ alkyl and
X is O or —OH, H;
provided that $R^2$, $R^3$, $R^4$, $R^5$ and $R^6$ are not simultaneously hydrogen, and $R^3$ is not Cl when $R^5$ is acetoxy;
or the pharmaceutically acceptable salt thereof.

In a fourth embodiment of this invention, the inhibitors of farnesyl-protein transferase are novel compounds of the formula I wherein:
$R^1$ is

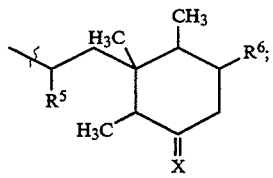

$R^2$ is hydrogen, formyl or $C_{1-4}$ alkyl;
$R^3$ is hydrogen or halogen;
$R^4$ is hydrogen, $C_{1-4}$ alkyl or acetyl;
$R^5$ is selected from:
 a) hydrogen; and
 b)

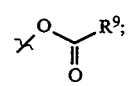

$R^6$ is hydrogen, $C_{1-4}$ alkyl or acetoxy;
$R^7$ is hydrogen or acyl;
$R^8$ is hydrogen or $C_1-C_6$ alkyl;
$R^9$ is $C_1-C_6$ alkyl; and
provided that $R^2$, $R^3$, $R^4$, $R^5$ and $R^6$ are not simultaneously hydrogen, and $R^3$ is not Cl when $R^5$ is acetoxy;
or the pharmaceutically acceptable salt thereof.

The following are specific examples of the compounds of the instant invention:

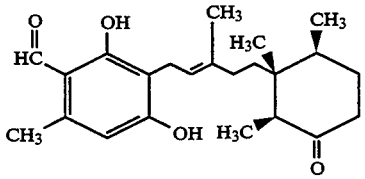   1

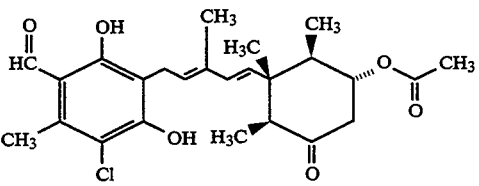   2

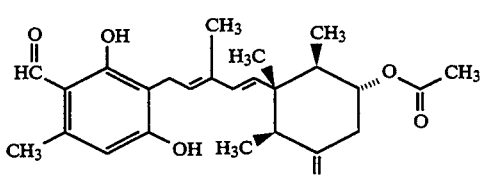   3

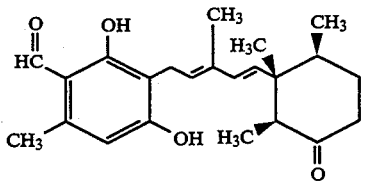   4

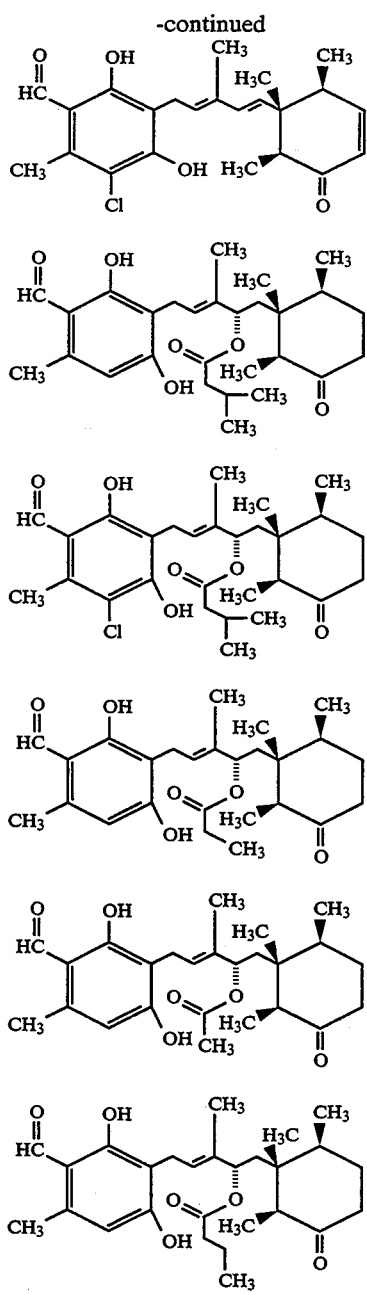

or the pharmaceutically acceptable salt thereof.

The following compounds of the instant invention are synthetic analogs of Compound 1:

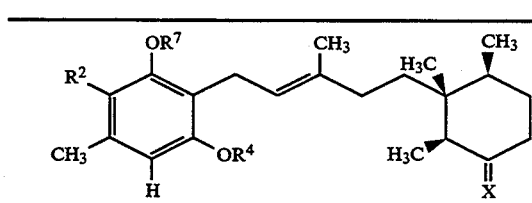

| COMPOUND | R² | R⁴ | R⁷ | X |
|---|---|---|---|---|
| 11 | —CHO | Ac | Ac | O |
| 13 | —CHO | —CH₃ | H | O |
| 15 | —CH₂OH | H | H | OH,H |
| 16 | —CH₃ | H | H | O |
| 17 | —CH₃ | H | H | OH,H |
| 18 | —CH₂OH | H | H | O |
| 19 | —CHO | (t-Bu)Me₂Si— | H | O |
| 20 | —CO₂CH₃ | H | H | O |
| 21 | —CHO | —MOM | —MOM | O |
| 24 | H | H | H | O |

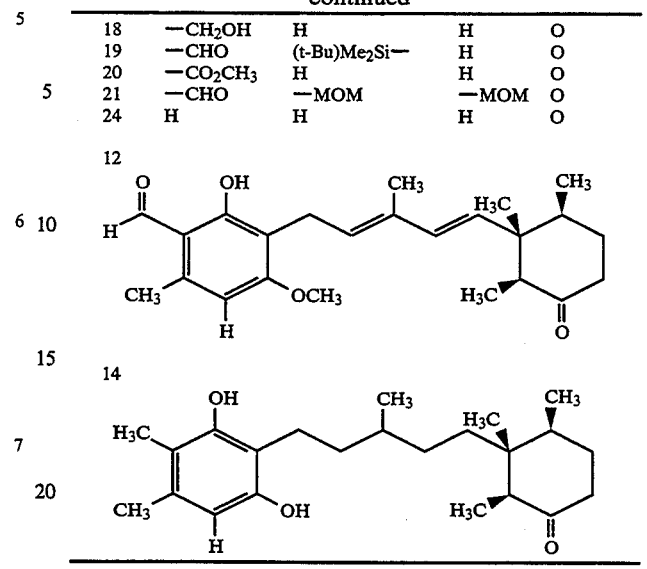

or the pharmaceutically acceptable salt thereof.

The following compounds are the preferred compounds of the instant invention:

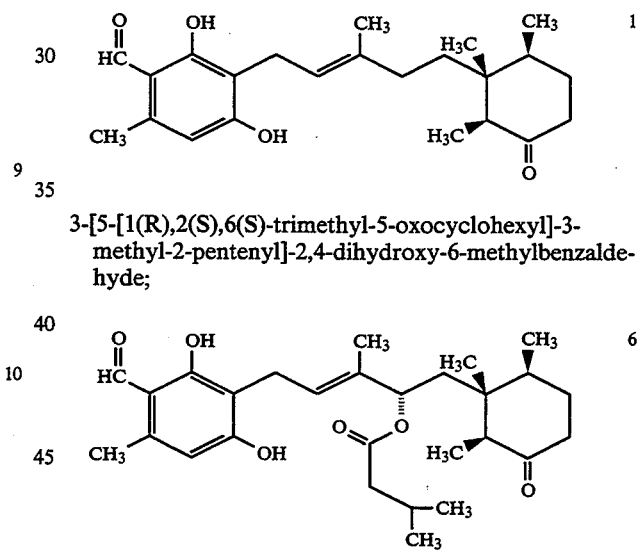

3-[5-[1(R),2(S),6(S)-trimethyl-5-oxocyclohexyl]-3-methyl-2-pentenyl]-2,4-dihydroxy-6-methylbenzaldehyde;

3-[5-[1(R),2(S),6(S)-trimethyl-5-oxocyclohexyl]-3-methyl-4(S)-[3-methylbutanoyloxy]-2-pentenyl]-2,4-dihydroxy-6-methylbenzaldehyde; and

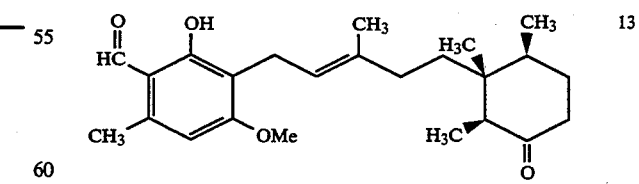

3-[5-[1(R),2(S),6(S)-trimethyl-5-oxocyclohexyl]-3-methyl-2-pentenyl]-2-hydroxy-4-methoxy-6-methyl-benzaldehyde.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^1$, $R^2$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

The pharmaceutically acceptable salts of the compounds of this invention include the conventional nontoxic salts of the compounds of this invention. For example, such conventional nontoxic salts include those having an alkali metal cation such as sodium or potassium. Other pharmaceutically acceptable cations which form salts may be calcium, magnesium, zinc, ammonium, or alkylammonium cations such as tetramethylammonium, tetrabutylammonium, choline, triethylhydroammonium, meglumine, triethanolhydroammonium, and the like.

Generally, the salts are prepared by reacting the compound of the invention with stoichiometric amounts or with an excess of the desired salt-forming inorganic or organic base in a suitable solvent or various combinations of solvents.

The compounds 1-9 are prepared in an aerobic fermentation procedure employing a novel culture, MF5710, identified as *Cylindocarpon lucidurn*. Although the use of this organism is specifically described. herein, mutants of the above described organism are also capable of producing the compounds of this invention.

The culture MF5710 is that of a fungus, *Cylindocarpon lucidum*, isolated from dried cow dung near Weed, Lincoln National Forest, Otero County, N.M. This culture has been deposited with the American Type Culture Collection at 12301 Parklawn Drive, Rockville, Md. 20852 as ATCC 74261.

The culture MF5710, identified as *Cylindocarpon lucidum*, exhibits the following morphological features:

Colonies growing moderately fast on potato-dextrose agar (D. Brayford. 1992. In Methods for Research on Soilbome Phytopathogenic Fungi. Edited by L. L. Singleton, J. D. Mihail & C. M. Rush. American Phytopathological Society Press, St. Paul, Minn. pp. 103–106), 25° C., 12 hr photoperiod, after 14 days attaining 29–31 mm in diameter, with abundant lanose to cottony aerial mycelium, moist, obscurely zonate, at first white but soon cream-colored to pale buff, Light Buff, Light-Ochraceous Buff (capitalized color names from Ridgway, R. 1912. Color Standards and Nomenclature, Wash., D.C.), dull yellowish brown, Warm Buff, toward center, forming dense stromata in older regions; stromata caespitose to confluent, dull brown, up to 2 mm in diameter; exuding droplets of clear to pale yellowish brownish liquid from aerial mycelium, reverse cream, dull yellowish brown, Ochraceous-Buff, to vinaceous brown, Russet, or dark brown, Mars Brown, obscurely zonate. Odor fragrant.

Colonies growing moderately fast on YME agar (Difco Laboratories), 25° C., 12 hr photoperiod, after 14 days attaining 25 mm in diameter, with velvety to cottony aerial mycelium, obscurely zonate, white to cream-colored, with margin even and submerged, similar in reverse. Odor fragrant.

No growth on YME at 37° C.

Colonies growing moderately fast on cornmeal agar (Difco Laboratories), 25° C., 12 hr photoperiod, after 14 days attaining 34–35 mm in diameter, translucent to pale cream-colored, appressed, with scant aerial mycelium, forming concentric zones of slimy sporodochia or conidiophores, margin even, submerged, with reverse translucent, zonate. Odor not distinctive.

Conidiophores arising from aerial hyphae or from agar surface, solitary, fasciculate, or loosely aggregated in sporodochia, abundant, 30–145 μm long, 3–6 gm wide at the base, sparsely to densely branched, with up to 4 tiers of branches, with each branch terminating in a single phialide. Conidiogenous cells enteroblastic, phialidic, 14.5–24 μm long, 2.5–4.5 μm wide, cylindrical or tapered towards the apex, sometimes constricted at the base, straight or curved at the base if in a lateral position, apex with periclinal thickenings and tubular, flared or ragged collarette, giving rise to masses of slimy macroconidia. Microconidia not observed. Chlamydospores not observed. Macroconidia 2–4 septate, but predominately 3-septate, cylindrical, consistently curved, with broadly rounded apices, smooth, hyaline, (30-)41–55(-60) gm long, 5–7 μm wide. Hyphae septate, branched, hyaline, or with intracellular yellow to yellowish brown pigments in age. Cells of stromatic tissues isodiametric, up to 10 gm in diameter, yellowish brown to brown. Asci or ascospores not observed.

The combination of hyaline, slimy conidia arising from phialides on branched conidiophores indicates that this fungus is the anamorphic state of an ascomycete of the Hypocreales. The cylindrical, septate conidia with rounded bases and apices, branched conidiophores, and light yellowish brown hyphal pigments are characteristic of the genus Cylindrocarpon. The absence of foot cells on the conidia eliminates the genus Fusarium as a possible identification. Within the genus Cylindrocarpon, this isolate can be placed in Booth's group 2 because it does not form chlamydospores or microconidia (C. Booth. 1966. The genus Cylindrocarpon. Commonwealth Mycological Institute Paper 104:1–56). Cylindrocarpon lucidum is distinguished from other species in Booth's group 2 by the yellowish to yellowish brown pigments and moderately wide conidia that are 3–5 septate. MF5710 generally conforms to Booth's original description of the species, as well as to the description provided by Samuels et al. (Samuels, G. A., Doi, Y. & Rogerson, C. T. 1990. Hypocreales. Mem. New York Bot. Gard. 59: 6–108), the only significant difference in MF5710 being the formation of sterile stromatic tissues in old cultures grown on potato-dextrose agar.

Compounds of this invention can be obtained by culturing the above noted microorganism in aqueous nutrient media containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone, corn steep liquor, distillers solubles, malt extracts and the like. Inorganic nitrogen sources such as ammonium salts (eg. ammonium nitrate, ammonium sulfate, ammonium phosphate, etc.) can also be used. The various sources of nitrogen can be used alone or in combination in amounts ranging between 0.2 to 50 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as polyethylene glycol or silicone may be added, especially if the culture medium foams seriously.

The preferred process for production of compounds of this invention consists of inoculating spores or mycelia of the producing organism into a suitable medium and then cultivating under aerobic condition.

The fermentation procedure generally is to first inoculate a preserved source of culture into a nutrient seed medium and to obtain, sometimes through a two step process, growth of the organism which serves as seed in the production of the active compounds. After inoculation, the flasks are incubated with agitation at temperature ranging from 20° to 30° C., preferably 25° to 28° C. Agitation rates may range up to 400 rpm, preferably 200 to 220 rpm. Seed flasks are incubated over a period of 2 to 10 days, preferably 2 to 4 days. When growth is plentiful, usually 2 to 4 days, the culture may be used to inoculate production medium flasks. A second stage seed growth may be employed, particularly when going into larger vessels. When this is done, a portion of the culture growth is used to inoculate a second seed flask incubated under similar conditions but employing shorter time.

After inoculation, the fermentation production medium is incubated for 3 to 30 days, preferably 4 to 22 days. The fermentation is conducted aerobically at temperatures ranging from 20° to 40° C. To obtain optimum results, the temperatures are in the range of 22° to 28° C., most preferably 24° to 26° C. The pH of the nutrient medium suitable for producing the active compounds is in the range of 3.5 to 8.5, most preferably 5.0 to 7.5. After the appropriate period for production of the desired compound, fermentation flasks are harvested and the active compound(s) isolated.

A mixture of an alcoholic solvent and an oxygenated solvent, such as an ester or a ketone, is employed to extract a compound(s) of this invention from the solid fermentation medium.

The mixture is vigorously stirred and filtered, and the filtrate is concentrated under reduced pressure. Water is added to the concentrate and the pH is adjusted to about 3 with a mineral acid. The aqueous concentrate is then repeatedly extracted with a water immiscible oxygenated solvent. The water immiscible organic layer is removed and evaporated to dryness. The residue is then generally subjected to several separation steps such as adsorption and partition chromatography, and precipitation. For each separation step, fractions are collected and combined based on results from an assay and/or HPLC/TLC analysis.

The preferred solvent for extraction of the solid fermentation is a 1:1 mixture of methanol and 2-butanone. After concentrating the initial extract and diluting with water, the preferred partitioning solvent is dichloromethane.

The chromatographic separations may be carded out by employing conventional column chromatography with ionic or nonionic absorbents or resins. Silica gel, such as that available from E. Merck, is the preferred adsorbent. When silica gel is the adsorbent, an alcohol/chlorohydrocarbon/organic acid mixture such as methanol/chloroform/acetic acid/water is useful as an eluant. For reverse phase chromatography, the preferred adsorbent is a C8 bonded phase silica gel. The preferred eluant for reverse phase chromatography is a mixture of acetonitrile and water buffered at a low pH, such as 0.1% phosphoric acid, or trifluoroacetic acid. Ionic resins such as Dowex-1 (Cl$^-$) or Dowex-50 (Ca$^{++}$) are also useful in the purification.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glucamine, lysine, arginine, omithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. The salts included herein encompass those wherein one, or both of the carboxyl groups are in the salt form.

The intrinsic famesyl-protein transferase (FPTase) activity of representative compounds of this invention was measured by the assay as described below:

Famesyl-protein transferase (FPTase) from bovine brain was chromatographed on DEAE-Sephacel (Pharmacia, 0–0.8M NaCl gradient elution), N-octyl agarose (Sigma, 0–0.6M NaCl gradient elution), and a mono Q HPLC column (Pharmacia, 0–0.3M NaCl gradient). Ras-CVLS (Cys-Val-Leu-Ser) at 3.5 mM, 0.25 mM [$^3$H]FPP, and the indicated compounds were incubated with this partially purified enzyme preparation. FPTase inhibition data is a measurement of the ability of the test compound to inhibit Ras farnesylation in vitro.

The compounds of this invention may also be prepared according to the reactions as shown in the Reaction Schemes below, in addition to other standard manipulations such as ester hydrolysis, cleavage of protecting groups, etc., as may be known in the literature or exemplified in the experimental procedures.

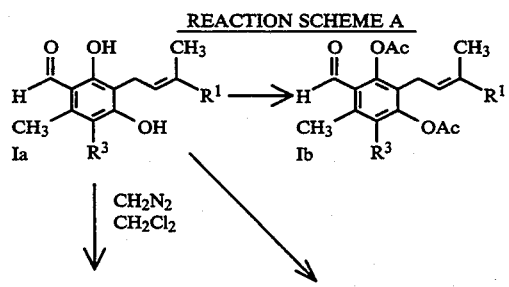

REACTION SCHEME A

-continued
REACTION SCHEME A

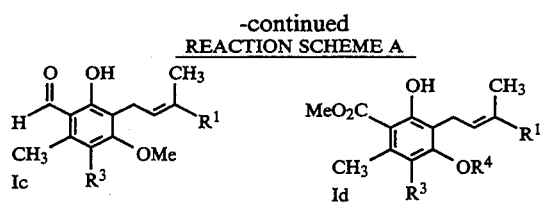

-continued
REACTION SCHEME C

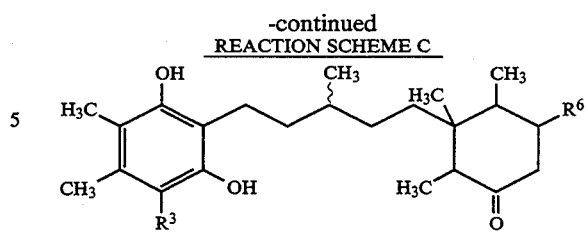

REACTION SCHEME D

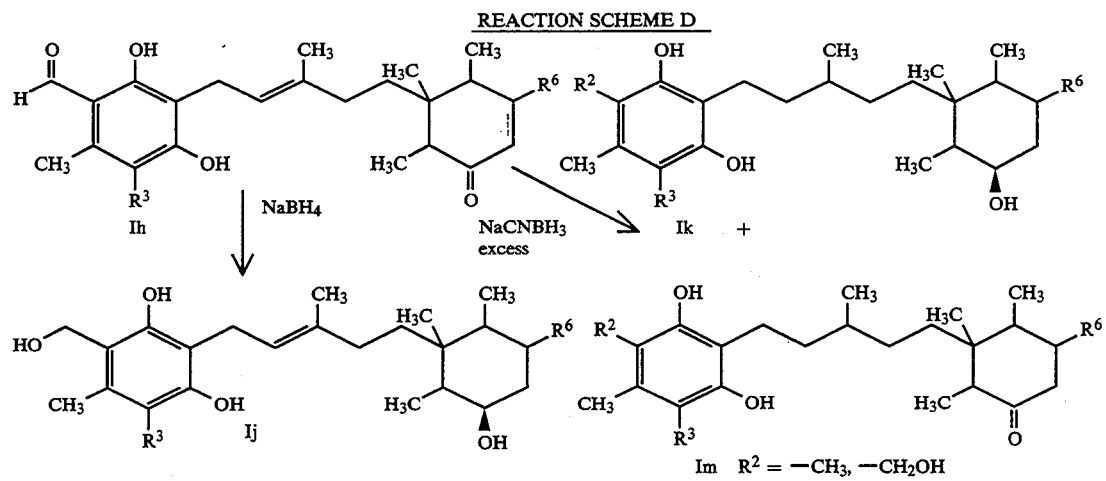

Im  $R^2 = -CH_3, -CH_2OH$

REACTION SCHEME B

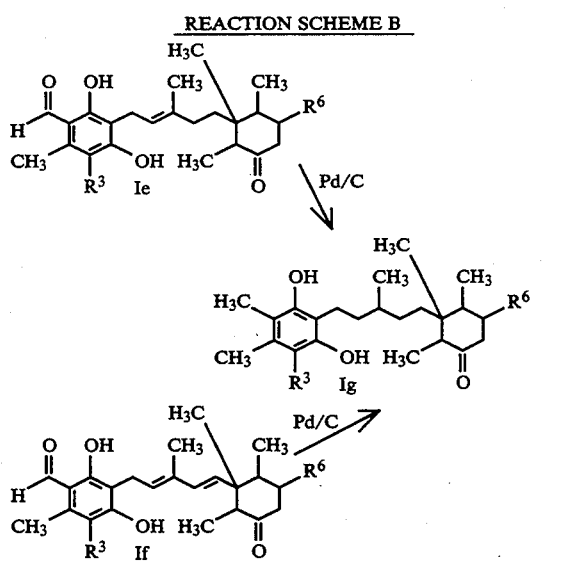

REACTION SCHEME C

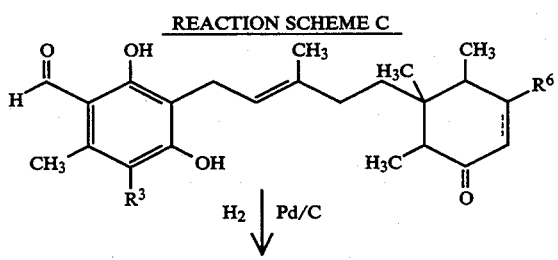

Synopsis of Reaction Schemes A–D:

The phenyl ring of the compounds of the instant invention may be derivatized as illustrated in Reaction Scheme A The diol Ia obtained by the fermentation described herein above is acylated under standard conditions, such as acetic anhydride in pyridine, acetyl chloride in pyridine and the like, to provide the bis acylated compound Ib. Treatment of the diol Ia with a methylating reagent, such as diazomethane and the like, provides the monomethyl ether Ic. Oxidation of the formyl group followed by in situ alcoholysis provides the ester Id.

As illustrated in Reaction Scheme B, hydrogenation of the compound Ie or If of the instant invention in the presence of a catalyst, such as palladium on carbon, platinum oxide and the like, reduces not only the ethylene moieties, but also the formyl moiety on the phenyl ring, providing compound Ig of the instant invention. In compounds having α, β unsaturation in the second ring, that double bond is also reduced, as illustrated in Reaction Scheme C.

Proteolytic reduction of the compound of formula Ih is reagent dependent as illustrated by Reaction Scheme D. Thus sodium borohydride reduction of Ih selectively reduces the formyl moiety (to a hydroxymethyl) and the ketone on the second ting. In contrast, sodium cyanoborohydride reduction provides a complex mixture of separable products wherein the formyl is reduced to either a hydroxymethyl or completely to a methyl group and the ketone moiety is either reduced or unchanged.

The compounds of this invention inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

EXAMPLES

Examples provided are intended to assist in a further understanding of the invention. Particular materials employed, species and conditions are intended to be further illustrative of the invention and not limitative of the reasonable scope thereof.

EXAMPLE 1

Preparation of Compounds of 1-9 by Fermentation

A. Culturing MF 5710

MF5710 cultures were maintained as mixtures of spores and hyphae in sterile soil and stored at 4° C. until ready for use. Seed cultures were inoculated by using a small portion of the preserved soil aseptically transferred into a 250 mls Erlenmeyer flask containing 50 mls of seed medium of the following composition (in g/liter); corn steep liquor, 5.0; tomato paste, 40.0; oat flour, 10.0; glucose, 10.0; and trace elements solution, 10 ml/liter (consisting of, in g/liter: $FeSO_4 \cdot 7H_2O$, 1.0; $MnSO_4 \cdot 4H_2O$, 1.0; $CuCl_2 \cdot 2H_2O$, 0.025; $CaCl_2 \cdot 2H_2O$, 0.1; $H_3BO_3$, 0.056; $(NH_4)_6MoO_{24} \cdot 4H_2O$, 0.019; $ZnSO_4 \cdot 7H_2O$, 0.2; dissolved in 0.6N HCl). The pH of the medium was adjusted to 6.8 by addition of NaOH before sterilization. Seed medium was prepared using distilled water and was dispensed into Erlenmeyer flasks that were capped with cotton plugs before being autoclaved at 121C for 20 minutes. Seed cultures were incubated at 25° C., on a gyrotory shaker (220 rpm, 5.1 cm throw) for 74 hours prior to inoculation of fermentation flasks.

Fermentations were performed on solid substrate and liquid production media. The solid substrate production medium was formulated as follows: millet, 15.0 g/250 ml Erlenmeyer flask to which was added 15 mls of 0.5 g yeast extract, 0.1 g sodium tartrate, 0.5 g sucrose, 0.5 g alfalfa, 0.1 ml corn oil, and 0.01 g $FeSO_4 \cdot 7H_2O$. Solid substrate production flasks were capped with cotton plugs and sterilized at 121 ° C. for 15 minutes. Immediately prior to inoculation, distilled water (15.0 mls) was added to each flask, the flasks were resterilized at 121 ° C. for 20 minutes and then cooled. Each production flask was inoculated with 2.0 ml vegetative seed growth mixed throughout the solid substrate. The production flasks were incubated without agitation at 25° C. for 21 days. Individual fermentation flasks were extracted to determine RASIT activity: one flask with 45 mls MeOH (70%) and another flask with 50 mls methyl ethylketone (MEK). The solid substrate fermentation batch was delivered unextracted for isolation.

The liquid production medium was formulated as follows (in g/liter): sucrose, 80.0; yellow corn meal, 50.0; and yeast extract, 1.0. This medium was prepared using distilled water; 50 mls medium was dispensed into 250 ml Erlenmeyer flasks that were capped with cotton plugs before being autoclaved at 121° C. for 20 minutes. Production flasks were inoculated with 2.0 mls vegetative seed growth and were incubated at 25° C., on a gyrotory shaker (220 rpm, 5.1 cm throw) for 21 days. At time of harvest, liquid fermentation flasks were homogenized and pooled. Samples were taken from this pool, extracted with MeOH or MEK, and assayed for RASIT activity. Remaining pooled whole broth was delivered for isolation.

B. Isolation of Active Compounds:

The fermentation whole broth (1.9 L) of *Cylindocarpon lucidum* (MF 5710) described above was extracted with methyl ethyl ketone (1.0 L) by shaking on a shaker at room temperature for 2 hours. Celite was added to the agitated thick mixture and was filtered using sintered glass funnel. The filtrate was transferred in to a separatory funnel and and the organic phase was separated. The aqueous layer was washed with 400 ml of methyl ethyl ketone. The combined organic phases were concentrated to a small volume on a rotary evaporator under reduced pressure and then lyophilized to remove residual water. The residue thus obtained was suspended in 100 mL methanol and filtered. The filtrate contained all of the Ras farnesyl-protein transferase activity. Methanol was removed from filtrate under reduced pressure to give 6.5 g of dark colored viscous gum.

The crude gum was dissolved in 50 mL methanol and was chromatographed over a Sephadex LH-20 (2.0 L) column in methanol. Column was eluted with methanol at a flow rate of 10 ml/minutes. Active components started eluting after 1350 mL elution volume of methanol and were pooled in six successive fractions (100 mL each) as follows: Fraction A (0.53 g), B (0.7 g), C (1.07 g), D (1.62 g), E (0.73 g) and F (0.14 g).

Fraction D was crystallized from acetone to give colorless rosettes of 90% pure Compound I which was recrystallized from hot methanol to give colorless needles of pure Compound 1.

Fractions A and B (1.23 g) were combined and chromatographed on a silica gel flash column (2×20 cm). Elution of the column with 10 to 30% ethyl acetate-hexane gave following compounds as amorphous solids listed in order of their elution: Compound 7, Compound 6, Fraction G (112 mg) and some other compounds.

Fraction G (112 mg) was rechromatographed on reversed phase preparative Whatman Partisil 10 (C-18) HPLC column (22×250 nun) and eluted initially for 10 min with 50% acetonitrile in water followed by a gradient to 60% acetonitrile over 60 minutes at a flow rate of 10 mL/minutes which gave, after lyophilization, powders of Compound 9 ($t_R$ 30 min), Compound 8 ($t_R$ 35 min), Compound 10 ($t_R$ 42 min), and Compound 6 ($t_R$ 48.7 min).

Fraction C (250 mg) was chromatographed over a similar Whatman Partisil-10 column with 50% acetonitrile-water eluting for 20 minutes followed by a gradient of 70% acetonitrile over 80 minutes at 10 mL/minutes. The fractions thus eluted were freeze dried to give amorphous powders of Compound 3 ($t_R$ 37.1 min), Compound 4 ($t_R$ 41 min), Compound I ($t_R$ 43 min), and Compound 2 ($t_R$ 52 min).

Crystallization of fraction E from methanol gave additional amounts of Compound I and chromatography of the mother liquor on a flash silica gel column (2×20 cm) and elution with 10 to 30% ethyl acetate in hexane gave other compounds.

Fraction F (130 mg) was chromatographed on a 50 cc silica gel column and eluted with 5 to 15% acetone in hexane to give fraction H (3.3 mg) which was chromatographed on a Whatman Partisil-10 22×250 mm HPLC column and eluted with a 60 minute gradient of 50 to 70% acetonitrile-water at a flow rate of 10 mL/min. The fractions eluted at 30 minutes after lyophilization yielded amorphous solid of Compound 5.

Spectral Data:

Compound 1

Mass Spectra: HREIMS (m/z): 372.2414 (M+, calcd. for $C_{23}H_{32}O_4$: 372.2300)

C-13 NMR (CDCl$_3$)δ: 214.48, 192.94, 163.71, 162.26, 141.93, 138.49, 121.31, 113.25, 111.92, 110.66, 50.52, 43.56, 41.55, 36.11, 35.64, 32.67, 30.97, 21.24, 17.97, 16.48, 15.33, 15.02, 7.57.

$^1$H NMR (CDCl$_3$) δ:0.57 (3H, s), 0.91 (3H, d, J=6.6 Hz), 0.88 (3H, d, J=6.8 Hz), 1.40 (2H, m), 1.60 (1H, m), 1.80 (1H, m), 1.82 (1H, m), 1.83 (3H, d, J=1.2 Hz), 1.98 (1H, m), 2.00 (1H, m), 2.34 (2H, m), 2.45 (1H, m), 2.48 (3H, d, J=0.6 Hz), 3.38 (2H, d, J=6.9 Hz), 5.28 (1H, qt, J=6.9, 1.2 Hz), 6.23 (1H, q, J=0.6 Hz), 6.54 (1H, brs), 10.07 (1H, s), 11.71 (1H, brs).

Compound 2

Mass Spectra: HREIMS (m/z): 462.1723 (M+, calcd. for $C_{25}H_{31}ClO_6$: 462.1803)

C-13 NMR (CDCl$_3$)δ: 8.83, 11.51, 12.43, 12.61, 14.46, 21.02, 22.23, 45.36, 45.54, 47.20, 53.85, 73.64, 111.50, 113.15, 113.67, 128.26, 133.76, 134.20 (2C), 137.82, 156.11, 162.20, 170.05, 193.20, 207.81.

$^1$H NMR (CDCl$_3$)δ: 0.74 (3H, s), 0.87 (3H, d, J=6.6 Hz), 0.84 (3H, d, J=6.6 Hz), 1.80 (1H, m), 1.92 (3H, s), 2.00 (1H, m), 2.06 (3H, s), 2.40 (1H, dd, J=12.6, 6.3 Hz), 2.49 (1H, m), 2.61 (3H, s), 2.87 (1H, dd, J=13.5, 5.7 Hz), 3.54 (2H, d, J=7.5 Hz), 4.90 (1H, dd, J=5.7, 11.1 Hz), 5.32 (1H, J=16.2 Hz), 5.5 (1H, t, J=6.9 Hz), 5.92 (1H, d, J=15.9 Hz), 6.39 (1H, brs), 10.15 (1H, s), 12.71 (1H, s).

Compound 3

Mass Spectra: HREIMS (m/z): 428.2287 (M+, calcd. for $C_{25}H_{32}O_6$: 428.2198)

C-13 NMR (CDCl$_3$)δ:8.84, 11.50, 12.43, 12.71, 17.96, 21.02, 21.32, 45.32, 45.58, 47.19, 53.80, 73.62, 110.41, 111.81, 113.46, 128.24, 133.84, 134.75, 142.09, 161.34, 163.77, 170.09, 192.99, 207.80.

$^1$H NMR (CDCl$_3$) δ:0.74 (3H, s), 0.87 (6H, d, J=6.9 Hz), 1.93 (3H, s), 2.00 (1H, m), 2.07 (3H, s), 2.41 (1H, dd, J=13.0, 6.7 Hz), 2.47 (1H, m), 2.50 (3H, s), 2.88 (1H, dd, J=13.5, 5.7 Hz), 3.50 (2H, d, J=7.5 Hz), 4.90 (1 H, dt, J=5.7, 11.0 Hz), 5.36 (1 H, d, J=16.2 Hz), 5.54 (1H, t, J=7.5 Hz), 5.80 (1H, brs), 5.94 (1H, d, J=15.9 Hz), 6.2 (1H, s), 10.09 (1H, s), 12.71 (1H, s).

Compound 4

Mass Spectra: HREIMS (m/z): 370.2161 (M+, calcd. for $C_{23}H_{30}O_4$: 370.2144)

C-13 NMR (CDCl$_3$) δ: 8.89, 10.34, 12.71, 16.29, 17.96, 21.32, 31.12, 0.82, 41.56, 48.51, 53.57, 110.48, 111.87, 113.39, 127.51, 132.86, 135.14, 136.17, 142.03, 161.59, 163.76, 192.97, 211.50.

$^1$H NMR (CDCl$_3$) δ: 0.71 (3H, s), 0.82 (3H, d, J=6.9 Hz), 0.84 (3H, d, J=6.6 Hz), 1.63 (2H, m), 1.80 (1H, m), 1.93 (3H, s), 2.40 (3H, m), 2.49 (3H, s), 3.50 (2H, d, J=7.2 Hz), 5.41 (1H, d, J=16.2 Hz), 5.52 (1H, t, J=6.9 Hz), 5.92 (1H, d, J=16.2 Hz), 6.06 (1H, brs), 6.21 (1H, s), 10.08 (1H, s), 12.71 (1H, s).

Compound 5

Mass Spectra: HREIMS (m/z): 402.1701 (M+, calcd. for $C_{23}H_{27}ClO_4$: 402.1598)

$^1$H NMR (CDCl$_3$) δ:0.80 (3H, s), 0.95 (3H, d, J=6.8 Hz), 0.97 (3H, d, J=7.6 Hz), 1.93 (3H, brs), 2.45 (1H, q, J=6.8 Hz), 2.60 (3H, s), 2.63 (1H, m), 3.54 (2H, d, J=7.2 Hz), 5.42 (1H, d, J=16 Hz), 5.54 (1H, brt, J=7.2 Hz), 5.98 (1H, d, J=16 Hz), 5.99 (1H, d, J=10 Hz), 6.36 (1H, brs), 6.55 (1H, dd, J=10, 2 Hz), 10.15 (1H, s), 11.71 (1H, brs).

Compound 6

Mass Spectra: HREIMS (m/z): 472.2824 (M+, calcd. for $C_{28}H_{40}O_6$: 472.2824)

C-13 NMR (CDCl$_3$)δ: 8.00, 11.91, 15.39, 15.61, 17.92, 20.72, 22.32, 22.37, 25.70, 31.10, 36.70, 39.55, 41.46, 43.81, 44.08, 50.45, 75.90, 110.57, 111.36, 113.29, 125.17, 136.63, 142.01, 161.60, 163.75, 172.55, 192.93, 213.47.

$^1$H NMR (CDCl$_3$) δ: 0.56 (3H, s), 0.84 (3H, d, J=6.6 Hz), 0.93 (6H, d, J=6.3 Hz), 0.97 (3H, d, J=6.6 Hz), 1.54 (1H, dd, J=15.6, 3.6 Hz), 1.54 (1H, m), 1.79 (1H, m), 1.81 (3H, s), 1.85 (1H, dd, J=15.6, 7.5 Hz), 1.95 (1H, m), 2.10 (1H, m), 2.12 (2H, d, J=6.3 Hz), 2.18 (1H, m), 2.25 (1H, m), 2.47 (3H, s), 2.56 (1H, q, J=6.3 Hz), 3.32 (1H, dd, J=15, 6.9 Hz), 3.41 (1H, dd, J=15, 7.2 Hz), 5.34 (1H, dd, J=7.8, 3.6 Hz), 5.59 (1H, t, J=7.2 Hz), 6.07 (1H, brs), 6.17 (1H, s), 10.06 (1H, s), 12.68 (1H, s).

Compound 7

Mass Spectra: HREIMS (m/z): 506.2463 (M$^+$, calcd. for C$_{28}$H$_{39}$ClO$_6$: 506.2434)

C-13 NMR (CDCl$_3$) δ: 7.92, 11.87, 14.41, 15.37, 15.57, 21.53, 22.25, 22.31, 25.69, 30.85, 31.14, 36.59, 39.58, 41.44, 43.80, 44.04, 50.40, 75.54, 113.14, 113.32, 124.86, 135.38, 137.87, 156.25, 162.25, 172.17, 193.20, 213.25.

$^1$H NMR (CDCl$_3$) δ: 0.55 (3H, s), 0.81 (3H, d, J=6.9 Hz), 0.91 (6H, d, J=6.3 Hz), 0.95 (3H, d, J=6.9 Hz), 1.53 (1H, dd, J=15.9, 4.2 Hz), 1.54 (1H, m), 1.80 (1H, m), 1.81 (1H, dd, J=15.6, 7.8 Hz), 1.81 (3H, s), 1.94 (1H, m), 2.08 (1H, m), 2.13 (2H, d, J=6.6 Hz), 2.19 (1H, m), 2.25 (1H, m), 2.54 (1H, q, J=6.6 Hz), 2.59 (3H, s), 3.39 (2H, d, J=7.2 Hz), 5.36 (1H, dd, J=7.5, 3.6 Hz), 5.57 (1H, t, J=6.3 Hz), 6.30 (1H, brs), 10.13 (1H, s), 12.66 (1H, s).

Compound 8

Mass Spectra: HREIMS (m/z): 444.2614 (M$^+$, calcd. for C$_{26}$H$_{36}$O$_6$: 444.2510)

C-13 NMR (CDCl$_3$) δ: 8.00, 9.08, 11.77, 15.43, 15.57, 17.94, 20.74, 28.04, 31.11, 36.62, 39.50, 41.44, 44.10, 50.45, 76.21, 110.48, 111.51, 113.17, 125.57, 135.96, 141.98, 161.89, 163.79, 173.97, 192.80, 214.08.

$^1$H NMR (CDCl$_3$) δ: 0.55 (3H, s), 0.82 (3H, d, J=6.6 Hz), 0.96 (3H, d, J=6.6 Hz), 1.13 (3H, t, J=7.5 Hz), 1.53 (1H, m), 1.56 (1H, dd, J=15.6, 4.5 Hz), 1.78 (1H, m), 1.81 (3H, s), 1.83 (1H, dd, J=15.6, 7.2 Hz), 1.94 (1H, m), 2.18 (1H, m), 2.25 (1H, m), 2.32 (2H, q, J=7.5 Hz), 2.45 (3H, s), 2.56 (1H, q, J=6.6 Hz), 3.31 (1H, dd, J=15, 6.6 Hz), 3.40 (1H, dd, J=15, 6.6 Hz), 5.36 (1H, dd, J=7.2, 4.2 Hz), 5.60 (1H, t, J=6.9 Hz), 6.18 (1H, s), 6.88 (1H, brs), 10.04 (1H, s), 12.65 (1H, s).

Compound 9

Mass Spectra: HREIMS (m/z): 430.2470 (M$^+$, calcd. for C$_{25}$H$_{34}$O$_6$: 430.2354)

C-13 NMR (CDCl$_3$) δ: 8.02, 11.80, 15.42, 15.50, 17.94, 20.74, 21.33, 31.12, 36.67, 39.53, 41.44, 44.08, 50.45, 76.27, 110.52, 111.43, 113.24, 125.49, 136.20, 142.03, 161.74, 163.77, 170.51, 192.93, 213.82.

$^1$H NMR (CDCl$_3$) δ: 0.56 (3H, s), 0.83 (3H, d, J=6.6 Hz), 0.97 (3H, d, J=6.6 Hz), 1.55 (1H, dd, J=15.6, 4.5 Hz), 1.58 (1H, m), 1.79 (1H, m), 1.81 (3H, s), 1.83 (1H, dd, J=16.0, 7.5 Hz), 1.94 (1H, m), 2.05 (3H, s), 2.18 (1H, m), 2.25 (1H, m), 2.46 (3H, s), 2.56 (1H, q, J=6.3 Hz), 3.35 (1H, dd, J=14.7, 6.9 Hz), 3.41 (1H, dd, J=14.7, 6.9 Hz), 5.34 (1H, dd, J=7.5, 3.9 Hz), 5.60 (1H, t, J=6.9 Hz), 6.18 (1H, s), 6.51 (1H, brs), 10.05 (1H, s), 12.67 (1H, s).

Compound 10

Mass Spectra: HREIMS (m/z): 458.2768 (M$^+$, calcd. for C$_{27}$H$_{38}$O$_6$: 458.2667)

$^1$H NMR (CDCl$_3$) δ: 0.57 (3H, s), 0.84 (3H, d, J=6.3 Hz), 0.96 (3H, t, J=6.9 Hz), 1.14 (3H, d, J=6.9 Hz), 1.53 (1H, m), 1.56 (1H, dd, J=15.6, 4.5 Hz), 1.64 (2H, hexet, J=7.5 Hz), 1.78 (1H, m), 1.81 (3H, s), 1.85 (1H, dd, J=15.6, 7.2 Hz), 1.95 (1H, m), 2.20 (1H, m), 2.27 (2H, t, J=7.5 Hz), 2.30 (1H, m), 2.47 (3H, s), 2.56 (1H, q, J=7.2 Hz), 3.32 (1H, dd, J=15.6, 6.9 Hz), 3.39 (1H, dd, J=15.6, 7.2 Hz), 5.36 (1H, dd, J=8, 3.9 Hz), 5.59 (1H, brt, J=6.9 Hz), 6.06 (1H, brs), 6.18 (1H, s), 10.06 (1H, s), 12.69 (1H, s).

EXAMPLE 2

Preparation of Compound 11:

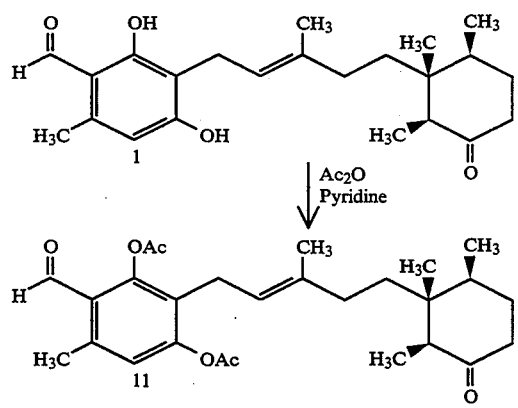

To a solution of Compound 1 (20 mg) in pyridine (0.2 mL) was added acetic anhydride (0.1 mL) and the solution was stirred at room temperature for 48 hrs. After completion of the reaction, pyridine and excess acetic anhydride was removed under stream of nitrogen and the residue was dried under vacuum. The crude product was purified on a pipette filled with silica gel and eluted with 20% ethyl acetate in hexane to give a chromatographically homogeneous Compound 11 as an amorphous powder.

$^1$H NMR (CDCl$_3$) δ: 0.57 (3H, s), 0.87 (3H, d, J=6.6 Hz), 0.90 (3H, d, J=6.9 Hz), 1.35 (3H, m), 1.61 (1H, m), 1.75 (3H, s), 1.82 (2H, m), 1.97 (1H, m), 2.30 (3H, s), 2.33 (2H, m), 2.35 (3H, s), 2.43 (1H, q, J=6.6 Hz), 2.61 (3H, s), 3.18 (2H, d, J=6.6 Hz), 5.01 (1H, t, J=6.6 Hz), 6.91 (1H, s), 10.27 (1H, s).

EXAMPLE 3

Preparation of Compounds 12 and 13:

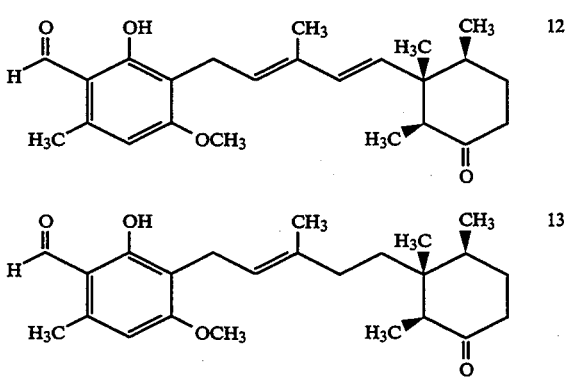

To a cooled (0° C.) solution of a 2:3 mixture of Compound 1 and Compound 4 in methylene chloride (1 mL) was added a ethereal solution (5 mL) of exess diazomethane and the solution was stirred at 0° C. overnight.

Reaction was complete and a polar (SiO$_2$: TLC, hexane-ethyl acetate, 7:3) product was formed. Solvents were carefully evaporated under stream of nitrogen and the products were purified on a silica gel column (1×10 cm) and eluted with 10% ethyl acetate-hexane. Both compounds were finally purified by chromatography on a reversed phase HPLC using Whatman ODS-(3 (22×250 mm) column. Elution with a 50% to 70% gradient of acetonitrile-water at 10 mL/min gave Compound 12 ($t_R$ 16 min) and Compound 13 ($t_R$ 18 min). The fractions were lyophilized to give amorphous colorless powder.

Compound 12

EIMS (m/z): 384 (M+).

$^1$H NMR (CDCl$_3$) δ: 0.69 (3H, s), 0.81 (3H, d, J=6.6 Hz), 0.84 (3H, d, J=6.6 Hz), 1.63 (2H, m), 1.90 (3H, s), 1.95 (1H, m), 2.38 (3H, m), 2.56 (3H, s), 3.45 (2H, d, J=7.2 Hz), 3.90 (3H, s), 5.34 (1H, d, J=15.9 Hz), 5.49 (1H, t, J=7.2 Hz), 5.89 (1H, d, J=15.9 Hz), 6.29 (1H, s), 10.13 (1H, s), 12.41 (1H, s).

Compound 13

EIMS (m/z): 386 (M+).

$^1$H NMR (CDCl$_3$) δ:0.55 (3H, s), 0.87 (3H, d, J=6.9 Hz), 0.90 (3H, d, J=6.6 Hz), 1.38 (2H, m), 1.63 (1H, m), 1.79 (3H, brs ), 1.83 (2H, m), 1.98 (2H, m), 2.31 (2H, m), 2.45 (1H, q, J=6.6 Hz), 2.56 (3H, s), 3.30 (2H, d, J=6.6 Hz), 3.89 (3H, s), 5.20(1H, t, J=6.6 Hz), 6.28 (1H, s), 10.12 (1H, s), 12.39 (1H, brs).

EXAMPLE 4

Hydrogenation of Compound 1:

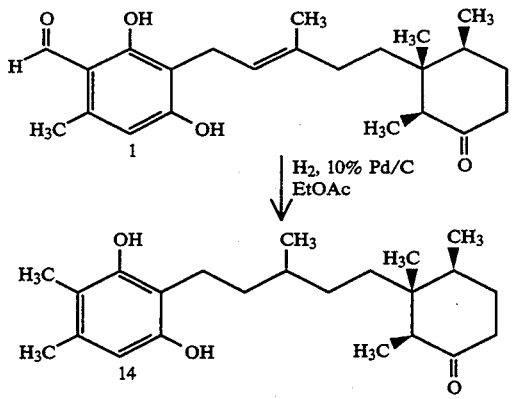

Palladium/carbon (10%, 10 mg) was added to a solution of Compound 1 (40 mg) in ethyl acetate (1.5 mL) and the reaction mixture was stirred under hydrogen filled balloon overnight. After completion of the reaction, catalyst was removed by filtration through Celite and the product was purified on a 1×10 cm silica gel column. Elution with 20% ethyl acetate-hexane yielded diastereomeric mixture of Compound 14 as an amorphous powder.

EIMS (m/z): 360 (M+).

$^1$H NMR (CDCl$_3$) δ: 0.57 (3H, s), 0.87, 0.91 (3H, d, J=6.6 Hz), 0.88, 0.90 (3H, d, J=6.9 Hz), 1.00 (3H, d, J=6.0 Hz), 1.21–1.36 (5H,m), 1.41 (1H, m), 1.61 (2H, m), 1.84 (1H,m), 2.00 (1H,m), 2.09 (3H, s), 2.19 (3H, s), 2.34 (2H, m), 2.47 (1H, brq, J=~5 Hz), 2.54–2.70 (2H, m), 4.70 (2H, brs, 2×OH), 6.25 (1H, s).

EXAMPLE 5

Reduction of Compound 1:

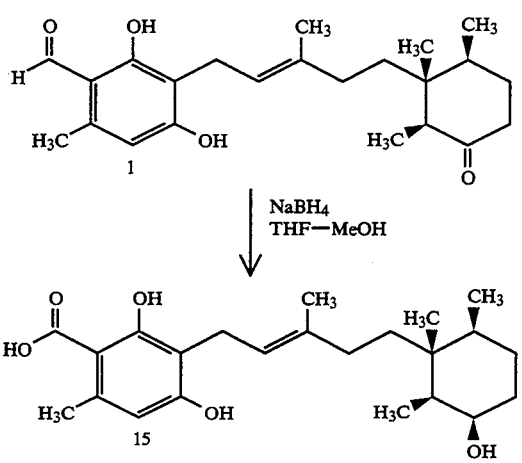

To a solution of Compound 1 (40 mg, 0.11 mmol) in a 3:2 mixture of tetrahydrofuran-methanol (1 mL) was added sodium borohydride (5.2 mg, 0.11 mmol) and the solution was stirred at ambient temperature for 10 minutes. The product diol was formed almost instantaneously. The reaction mixture was concentrated to dryness and ethyl acetate (100 mL) was added. The ethyl acetate solution was washed with water (2×50 mL), dried (Na$_2$SO$_4$), and evaporated under reduced pressure to give a gummy residue which was chromatographed on a 1×10 cm silica gel column. Elution of the column with 25% ethyl acetate-hexane afforded Compound 15 as an amorphous powder.

EIMS (m/z): 376 (M+).

$^{13}$C NMR (CDCl$_3$) δ: 12.40, 15.71, 16.49, 17.28, 19.12, 22.25, 25.51, 32.91, 33.89, 36.18, 36.53, 38.51, 39.48, 60.52, 73.29, 109.40, 112.13, 115.58, 121.51, 134.19, 139.28, 154.70, 155.39.

$^1$H NMR (CDCl$_3$) δ: 0.81 (3H, d, J=6.3 Hz),0.84 (3H, s), 0.95 (3H, d, J=7.5 Hz), 1.30 (3H,m), 1.41–1.63 (5H, m), 1.74–1.91 (2H, m), 1.83 (3H,s), 2.19 (3H,s), 3.40 (2H, d, J=6.9 Hz), 3.84 (1H, dd, J=3.0, 3.0 Hz), 4.84 (2H, brs), 5.27 (1H, t, J=6.9 Hz), 5.29 (1H, brs, OH), 6.22 (1H, s), 7.66 (1H, brs, OH).

EXAMPLE 6

Excess Sodium cyanoborohydride reduction of Compound 1:

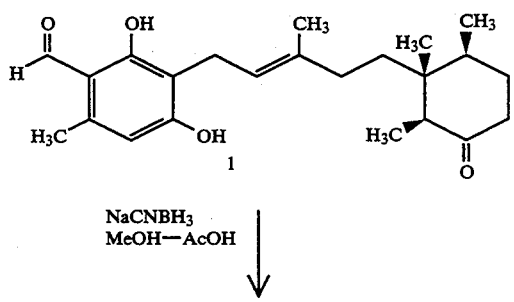

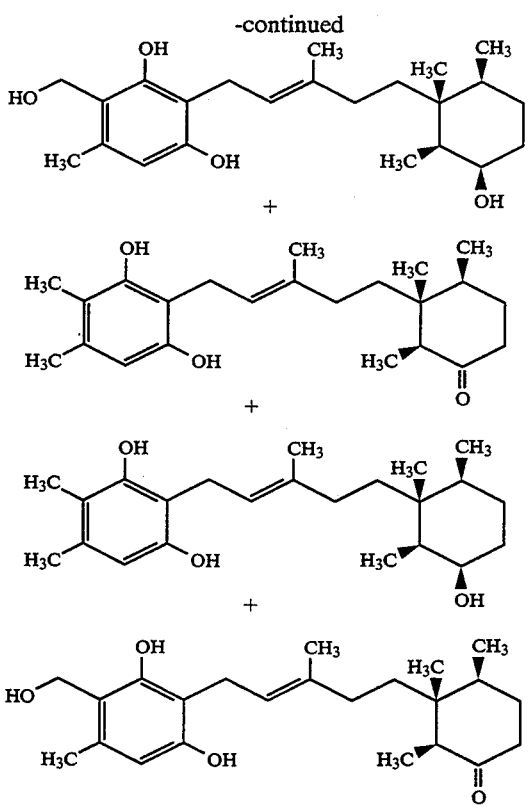

Sodium cyanoborohydride (10 mg, 0.16 mmol) was added to a solution of Compound 1 (16 mg, 0.043 mmol) in methanol (2 mL) and acetic acid (0.02 mL) and the solution was stirred overnight at room temperature. After all of the starting material was consumed, ethyl acetate (100 mL) was added to the reaction mixture, washed with water (2×50 mL), dried (Na$_2$SO$_4$) and evaporated under reduced pressure to give a mixture of four products. These products were purified on preparative silica gel plates (250g) developed in ethyl acetate-hexane (7:3). Four bands were eluted with acetone to provide Compounds 15-18, mostly as a gum.

EXAMPLE 7

Sodium cyanoborohydride (equimolar followed by excess amount) reduction of Compound 1.

To a solution of Compound 1 (70 mg, 0.19 mmol) in a mixture of tetrahydrofuran-methanol (1:1, 4 mL) and acetic acid (0.1 mL) was added sodium cyanoborohydride (11.9 mg, 0.19 mmol) and the solution was stirred overnight under nitrogen. The progress of the reaction was extremely slow and most of the starting material was left intact. Additional amounts of sodium cyanoborohydride (17.9 mg, 0.28 mmol) was added and reaction mixture was stirred for additional 24 hrs. Two major products (Compounds 16 and 17) were formed and starting material was consumed. The reaction mixture was worked up as described in the previous experiment and products were purified on a small silica gel column and eluted with 10 to 20% ethyl acetate-hexane to give clean Compounds 16 and 17.

Compound 16

EIMS (m/z): 358 (M+).
$^1$H NMR (CDCl$_3$) δ: 0.58 (3H, s), 0.88 (3H, d, J=6.9 Hz), 0.92 (3H, d, J=6.6 Hz), 1.34-1.46 (2H, m), 1.50-1.69 (2H, m), 1.79-2.10 (3H, m), 1.86(3H, brs ), 2.07 (3H, s), 2.19 (3H, s), 2.34 (2H, m), 2.45 (1H, q, J=6.6 Hz), 2.56 (3H, s), 3.41 (2H, d, J=7.5 Hz), 4.68 (1H, brs, OH), 5.08 (1H, brs, OH), 5.28 (1H, brt, J=6.9 Hz), 6.27 (1H, s).

Compound 17

EIMS (m/z): 360 (M+).
$^1$H NMR (CDCl$_3$) δ: 0.82 (3H, d, J=6.6 Hz), 0.84 (3H, s), 0.96 (3H, d, J=7.2 Hz), 1.27-1.40 (3H,m), 1.41-1.62 (5H, m), 1.74-1.91 (2H, m), 1.84 (3H,s), 2.08 (3H, s), 2.19 (3H,s), 3.40 (2H, d, J=6.9 Hz), 3.84 (1H, dd, J=2.7, 2.7 Hz), 4.69 (1H, brs, OH), 5.14 (1H, brs, OH), 5.25 (1H, t, J=6.9 Hz), 6.23 (1H, s).

Compound 18

EIMS (m/z): 374 (M+).
$^1$H NMR (CDCl$_3$) δ: 0.57 (3H, s), 0.88 (3H, d, J=6.6 Hz), 0.91 (3H, d, J=6.6 Hz), 1.30-1.65 (4H,m), 1.85 (3H,s), 1.87-2.1 (3H, m), 2.20 (3H,s), 2.32 (2H, m), 2.46 (1 H, q, J=7.2 Hz), 3.41 (2H, d, J=6.9 Hz), 4.88 (2H, brs), 5.05 (1H, brs, OH), 5.30 (1H, t, J=6.9 Hz), 6.23 (1H, s), 7.68 (1H, brs, OH).

EXAMPLE 8

Preparation of the Mono TBDMS ether of Compound 1:

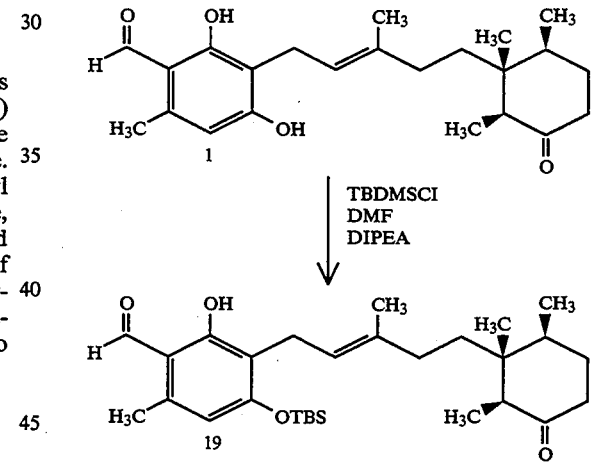

To a solution of Compound 1 (100 mg, 0.27 mmol) in dimethylformamide (1 mL) was added diethylisopropyl amine (0.21 mL, 1.2 mmol) followed by tert-butyldimethylsilyl chloride (121 mg, 0.8 mmol). The solution was stirred under nitrogen overnight. Icewater (50 ml) was added and the mixture was stirred for 20 minutes. The product was extracted with ethyl acetate (100 mL), washed sequentially with water, 10% aqueous citric acid, water, 10% aqueous sodium bicarbonate and water. The extract was dried over sodium sulfate, ethyl acetate was removed under reduced pressure and the residue crystallized from methanol to give colorless crystals of Compound 19.

Compound 19

EIMS (m/z): 486 (M+).
$^1$H NMR (CDCl$_3$) δ: 0.29 (6H, s), 0.56 (3H, s), 0.87 (3H, d, J=6.9 Hz), 0.90 (3H, d, J=6.9 Hz), 1.01 (9H, s), 1.30-1.65 (4H,m), 1.77 (3H, s), 1.82 (1H, m), 1.98 (2H, m), 2.31 (2H, m), 2.44 (1H, q, J=6.9 Hz), 2.49 (3H, s), 3.30 (2H, d, J=6.9 Hz), 5.19 (1H, t, J=6.6 Hz), 6.19 (1H, s), 10.11 (1H, s), 12.47 (1H, brs, OH).

EXAMPLE 9

Preparation of Compound 20:

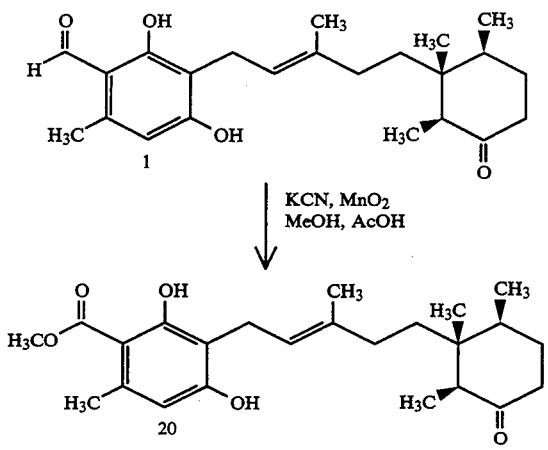

To a solution of Compound I (200 mg, 0.54 mmol) in methanol (8 mL) was added manganese dioxide (936 mg, 20 equivalent) and potassium cyanide (338 mg, 10 equivalent) followed by acetic acid (0.31 mL, 10 equivalent) and the mixture was stirred at room temperature under nitrogen overnight. Two (2) additional equivalents of potassium cyanide and acetic acid was added and the mixture was heated at 70° C. for 6 hrs. After completion of the reaction, the mixture was filtered through celite and the filtrate was diluted with 50 mL of ethyl acetate and washed with water, dried over sodium sulfate and evaporated under reduced pressure. The product mixture was chromatographed over a silica gel column and eluted with 20% ethyl acetate-hexane to give the methyl ester Compound 20 as an amorphous powder.

EIMS (m/z): 402 (M+)

$^1$H NMR (CDCl$_3$) δ: 0.57 (3H, s), 0.88 (3H, d, J=6.6 Hz), 0.91 (3H, d, J=6.6 Hz), 1.30–1.65 (4H,m), 1.84 (3H, s), 1.75'42.1 (3H, m), 2.32 (2H, m), 2.45 (1H, q, J=6.9 Hz), 2.46 (3H, s), 3.42 (2H, d, J=7.2 Hz), 3.92 (3H, s), 5.30 (1H, t, J=6.6 Hz), 5.66 (1H, brs, OH), 6.23 ( 1 H, s), 12.00 ( 1 H, brs, OH).

$^{13}$C NMR (CDCl$_3$) δ: 7.6, 15.12, 15.37, 16.52, 22.20, 24.02, 31.09, 32.83, 35.83, 36.28, 41.63, 43.59, 50.58, 51.73, 105.5, 111.34, 111.70, 121.84, 138.29, 140.88, 159.17, 162.79, 173.0, 213.0.

EXAMPLE 10

Preparation of the DiMOM ether of Compound 1:

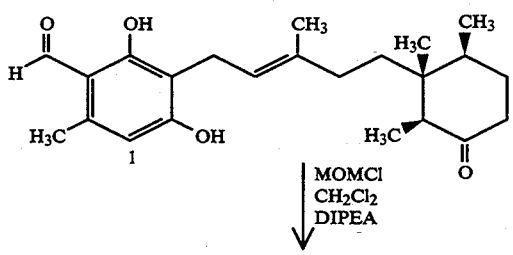

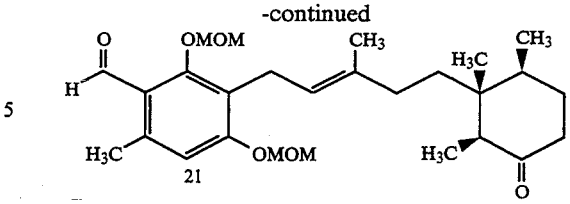

To a solution of Compound I (117 mg, 0.32 mmol) in CH$_2$Cl$_2$ (2 mL) was added diisopropyl amine (0.35 mL, 1.92 mmol) followed by addition of MOM chloride (0.15 mL, 1.92 mmol) and the solution was stirred at room temperature under nitrogen for 5 hrs. After completion of the reaction, ice was added followed by ethyl acetate (100 mL). The ethyl acetate layer was washed with water, 10% aqueous citric acid, water, dried (Na$_2$SO$_4$), and evaporated under reduced pressure to give crude product which was chromatographed over a small silica gel column and eluted with 5% ethyl acetate-hexane to provide Compound 21 as a colorless gum.

$^1$H NMR (CDCl$_3$) δ: 0.54 (3H, s), 0.85 (3H, d, J=6.6 Hz), 0.88 (3H, d, J=6.6 Hz), 1.35 (2H,m), 1.60 (2H, m), 1.78 (3H, s), 1.80 (1H, m), 1.95 (2H, m), 2.31 (2H, m), 2.45 (1H, q, J=6.6 Hz), 2.56 (3H, s), 3.46 (2H, d, J=6.9 Hz), 3.45 (3H, s), 3.57 (3H, s), 5.00 (2H, s), 5.15(1H, t, J=6.6 Hz), 5.24 (2H, s), 6.74 (1H, s), 10.36 (1H, s).

EXAMPLE 11

Oxidation of Compound 2 1:

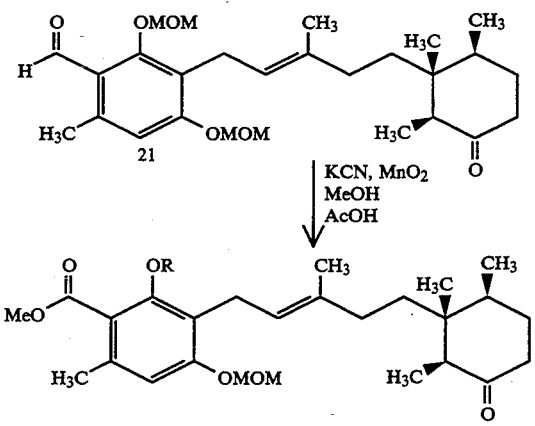

R = H, Compound 22
R = MOM, Compound 23

Following the procedure described in Example 9, Compound 21 (130 mg, 0.28 mmol) in 3 mL methanol was reacted with MnO$_2$ (486 mg, 20 eq), KCN (182 mg, 10 eq) and AcOH (0.13 mL, 8 eq) for 4 days. Two products were formed and were purified on preparative TLC using hexane-ethyl acetate (4:1). Bands were eluted (listed in order of their elution) with acetone to give Compounds 22 and 23, both as colorless gum.

Compound 22

$^1$H NMR (CDCl$_3$) δ: 0.55 (3H, s), 0.86 (3H, d, J=6.6 Hz), 0.89 (3H, d, J=6.9 Hz), 1.35 (2H,m), 1.63 (2H, m), 1.81 (3H, s), 1.80 (1H, m), 1.97 (2H, m), 2.31 (2H, m), 2.45 (1H, q, J=6.6 Hz), 2.50 (3H, s), 3.36 (2H, d, J=6.9 Hz), 3.46 (3H, s), 3.92 (3H, s), 5.23 (1H, t, J=6.6 Hz), 5.23 (2H, s), 6.47 (1H, s), 10.50 (1H, brs, OH).

27

Compound 23

¹H NMR (CDCl₃) δ: 0.55 (3H, s), 0.85 (3H, d, J=6.6 Hz), 0.88 (3H d, J=6.9 Hz), 1.35 (2H,m), 1.63 (2H, m), 1.77 (3H, s), 1.82 (1H, m), 1.96 (2H, m), 2.32 (2H, m), 2.44 (1H, q, J=6.6 Hz), 2.47 and 2.58 (3H, s), 3.35 (2H, brd, J=6.9 Hz), 3.44 (3H, s), 3.52 (3H, s), 3.88 (3H, s), 4.95 (2H, s), 5.18 (1H, t, J=6.6 Hz), 5.18 (2H, s), 6.73 (1H, s).

EXAMPLE 12

Hydrolysis of Compound 20:

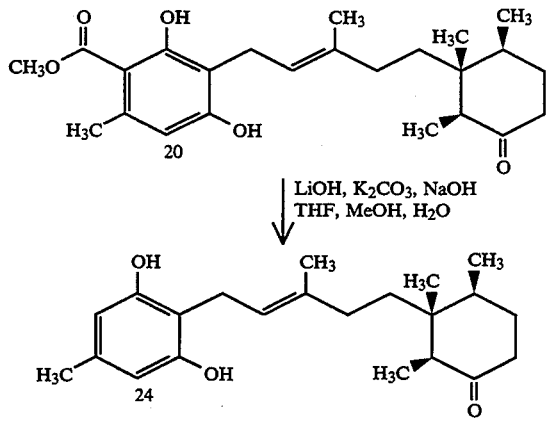

To a solution of Compound 20 (30 mg) in THF (3 mL), methanol (3 mL) and water (4 mL) was added LiOH (10 mg) and the solution was stirred at room temperature for 2 hrs. 20 mg of K₂CO₃ was added and stirring continued for another 2 hrs. NaOH (4N, 0.1 mL) was then added and the solution was heated at 70° C. for overnight. TLC analysis indicated that the starting material was consumed and the reaction mixture was acidified at −78° C. with dilute HCl. The products were extracted with ethyl acetate (2×50 mL), washed with water, dried (Na₂SO₄) and evaporated to give a complex mixture of products. These products were chromatographed on a reversed phase Whatman C-18 (9.4×250 nun) column and eluted with a gradient of 40 to 60% acetonitrile-water containing 0.2% TFA. Elution at 4 mL per minutes gave Compound 24 and numerous orange unidentified high molecular weight compounds.

Compound 24

EIMS (m/Z): 344 (M+).

¹H NMR (CDCl₃) δ: 0.57 (3H, s), 0.88 (3H, d, J=6.9 Hz), 0.91 (3H, d, J=6.6 Hz), 1.41 (2H,m), 1.80 (2H, m), 1.84 (3H, s), 1.90 (1H, m), 1.96 (2H, m), 2.22 (3H, s), 2.34 (2H, m), 2.45 (1H, q, J=6.6 Hz), 3.39 (2H, d, J=6.6 Hz), 4.92 (1H, s), 5.27 (1H, t, J=7.2 Hz), 6.24

EXAMPLE 13

In vitro inhibition of Ras farnesyl-protein transferase

Farnesyl-protein transferase (FPTase) from bovine brain was chromatographed on DEAE-Sephacel (Pharmacia, 0–0.8M NaCl gradient elution), N-octyl agarose (Sigma, 0–0.6M NaCl gradient elution), and a mono Q HPLC column (Pharmacia, 0–0.3M NaCl gradient). Ras-CVLS at 3.5 gM, 0.25 gM [3H]FPP, and the indicated compounds were incubated with either a partially purified bovine enzyme preparation or a recombinant human enzyme preparation. The FPTase data presented below in Table 1 reflects the ability of the test compound to inhibit RAS famesylation in vitro, as described in Pompliano, et al., Biochemistry 31, 3800 (1992).

TABLE 1

Inhibition of RAS farnesylation by compounds of this invention*

| Compound | IC₅₀(μM)* |
|---|---|
| 1 | 0.7 μM |
| 2 | 2.8 μM |
| 3 | 5.6 μM |
| 4 | 6.5 μM |
| 5 | 15.0 μM |
| 6 | 4.6 μM |
| 7 | 6.5 μM |
| 8 | 2.2 μM |
| 9 | 13.0 μM |
| 11 | 6.5 μM |
| 12 | 31 μM |
| 13 | 2.0 μM |
| 14 | 18.6 μM |
| 15 | 101 μM |
| 16 | 30.7 μM |
| 17 | >140 μM |
| 18 | 75 μM |
| 19 | >140 μM |
| 20 | >140 μM |
| 21 | >50 μM |
| 24 | 20 μM |

*(IC₅₀ is the concentration of the test compound which gives 50% inhibition of bovine brain FPTase under the described assay conditions)

What is claimed is:

1. A compound which inhibits farnesyl-protein transferase of the formula I:

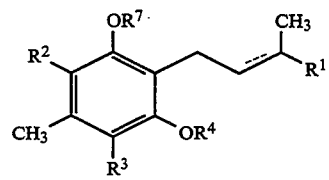

wherein:

R¹ is

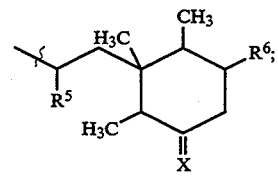

R² is hydrogen, formyl, C₁₋₄ alkyl, —CO₂R⁸ or —CH₂OH;

R³ is hydrogen or halogen;

R⁴ is hydrogen, C₁₋₄ alkyl, —CH₂OCH₃, t-Bu(CH₃)₂Si— or acetyl;

R⁵ is selected from:
  a) hydrogen; and
  b)

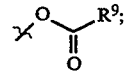

R⁶ is hydrogen, C₁₋₄ alkyl or acetoxy;
R⁷ is hydrogen, —CH₂OCH₃ or acyl;
R⁸ is hydrogen or C₁-C₆ alkyl;
R⁹ is C₁-C₆ alkyl and the dashed line represents either a bond, thereby creating a double bond, or the absence of a second bond; and
X is O or —OH, H;
provided that $R^2$, $R^3$, $R^4$, $R^5$ and $R^6$ are not simultaneously hydrogen, and $R^3$ is not Cl when $R^5$ is acetoxy;
or a pharmaceutically acceptable salt thereof.

2. The compound according to claim 1 having the formula I wherein:
$R^1$ is

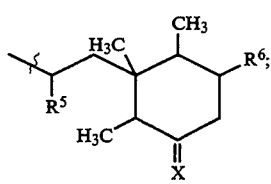

$R^2$ is hydrogen, formyl or $C_{1-4}$ alkyl;
$R^3$ is hydrogen or halogen;
$R^4$ is hydrogen, $C_{1-4}$ alkyl or acetyl;
$R^5$ is selected from:
a) hydrogen; and
b)

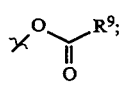

$R^6$ is hydrogen, $C_{1-4}$ alkyl or acetoxy;
$R^7$ is hydrogen or acyl;
$R^8$ is hydrogen or $C_1$-$C_6$ alkyl;
$R^9$ is $C_1$-$C_6$ alkyl and
provided that $R^2$, $R^3$, $R^4$, $R^5$ and $R^6$ are not simultaneously hydrogen, and $R^3$ is not Cl when $R^5$ is acetoxy;
or a pharmaceutically acceptable salt thereof.

3. The compound according to claim 1 which is selected from

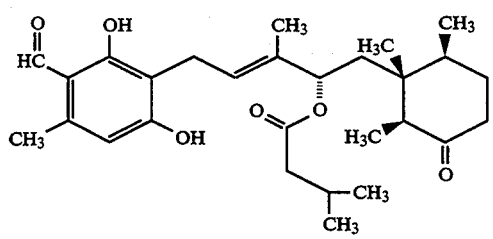

6

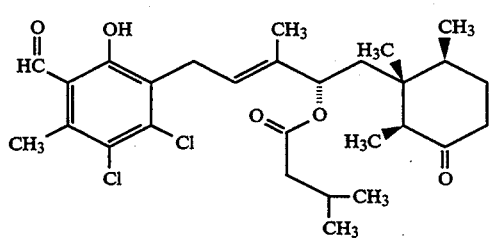

7

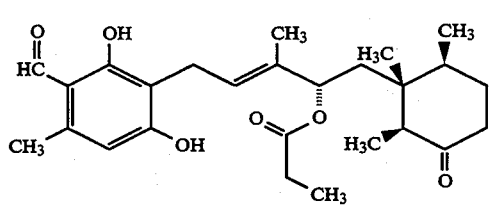

8

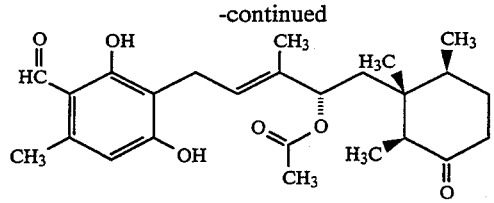

9 and

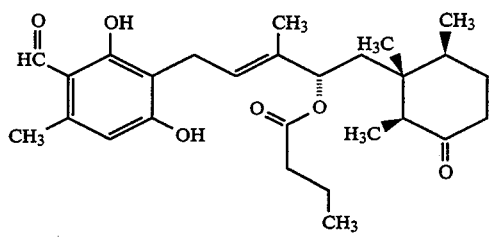

10 or a pharmaceutically acceptable salt thereof.

4. The compound according to claim I which is selected from:

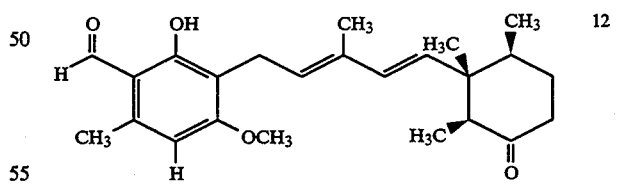

| COMPOUND | $R^2$ | $R^4$ | $R^7$ | X |
|---|---|---|---|---|
| 11 | —CHO | Ac | Ac | O |
| 13 | —CHO | —CH$_3$ | H | O |
| 15 | —CH$_2$OH | H | H | OH,H |
| 16 | —CH$_3$ | H | H | O |
| 17 | —CH$_3$ | H | H | OH,H |
| 18 | —CH$_2$OH | H | H | O |
| 19 | —CHO | t-BuMe$_2$Si- | H | O |
| 20 | —CO$_2$CH$_3$ | H | H | O |
| 21 | —CHO | —MOM | —MOM | O and |
| 24 | H | H | H | O; | or a pharmaceutically acceptable salt thereof.

5. The compound according to claim 1 which is selected from:

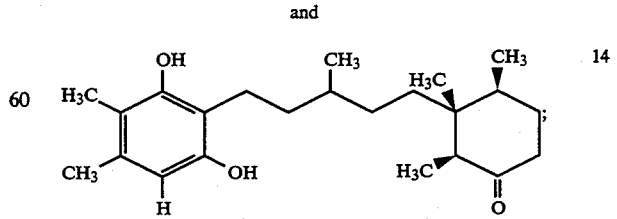

or a pharmaceutically acceptable salt thereof.

6. The compound according to claim 1 which is

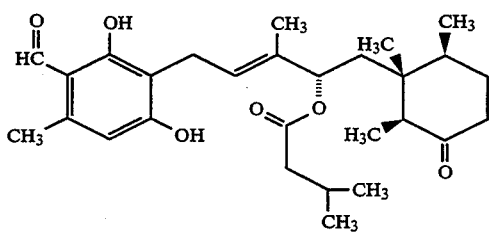

3-[5-[1(R),2(S),6(S)-trimethyl-5-oxocyclohexyl]-3-methyl-4(S)-[3-methylbutanoyloxy]-2-pentenyl]-2,4-dihydroxy-6-methylbenzaldehyde.

7. The compound according to claim 1 which is

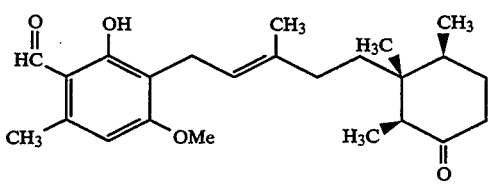

3-[5-[1(R),2(S),6(S)-trimethyl-5-oxocyclohexyl]-3-methyl-2-pentenyl]-2-hydroxy-4-methoxy-6-methylbenzaldehyde.

8. A method of inhibiting farnesyl-protein transferase which comprises administering to a mammal in need thereof a therapeutically effective amount of a compound of the formula I:

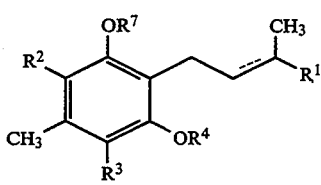

wherein:
$R^1$ is

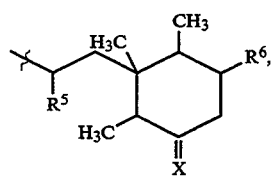

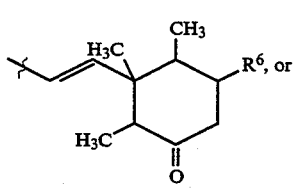

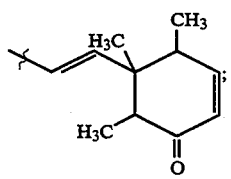

$R^2$ is hydrogen, formyl, $C_{1-4}$ alkyl, —$CO_2R^8$ or —$CH_2OH$;
$R^3$ is hydrogen or halogen;

$R^4$ is hydrogen, $C_{1-4}$ alkyl, —$CH_2OCH_3$, t-Bu(CH$_3$)$_2$Si— or acetyl;
$R^5$ is selected from:
  a) hydrogen; and
  b)

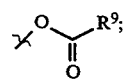

$R^6$ is hydrogen, $C_{1-4}$ alkyl or acetoxy;
$R^7$ is hydrogen, —$CH_2OCH_3$ or acyl;
$R^8$ is hydrogen or $C_1$–$C_6$ alkyl
$R^9$ is $C_1$–$C_6$ alkyl and
the dashed line represents either a bond, thereby creating a double bond, or the absence of a second bond; and
X is O or —OH, H;
or a pharmaceutically acceptable salt thereof.

9. The method according to claim 8 of inhibiting farnesyl-protein transferase which comprises administering to a mammal in need thereof a therapeutically effective amount of a compound of the formula I:

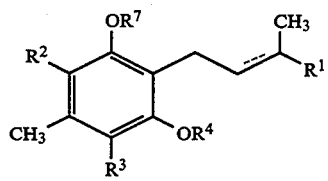

wherein:
$R^1$ is

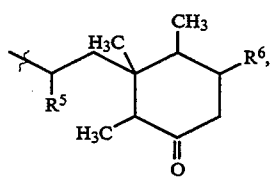

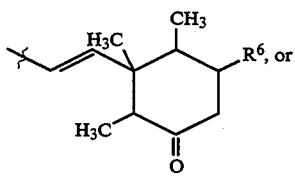

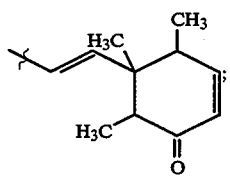

$R^2$ is hydrogen, formyl or $C_{1-4}$ alkyl;
$R^3$ is hydrogen or halogen;
$R^4$ is hydrogen, $C_{1-4}$ alkyl or acetyl;
$R^5$ is selected from:
  a) hydrogen; and
  b)

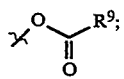

$R^6$ is hydrogen, $C_{1-4}$ alkyl or acetoxy;
$R^7$ is hydrogen or acyl;
$R^8$ is hydrogen or $C_1$–$C_6$ alkyl and
$R^9$ is $C_1$–$C_6$ alkyl;
or a pharmaceutically acceptable salt thereof.

10. The method according to claim 8 wherein the compound which is administered is selected from:

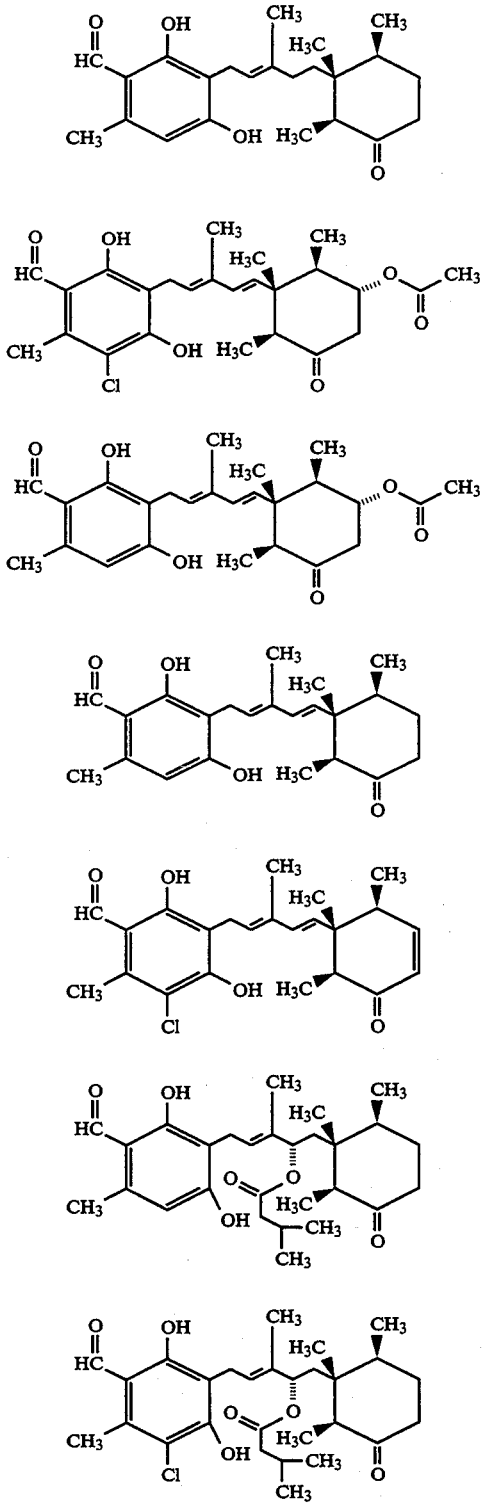

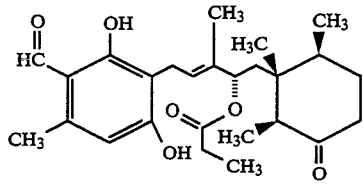

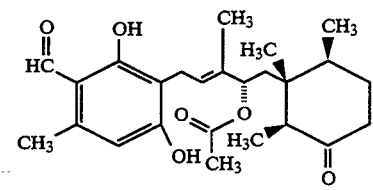

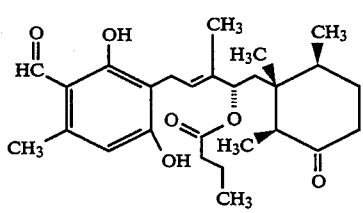

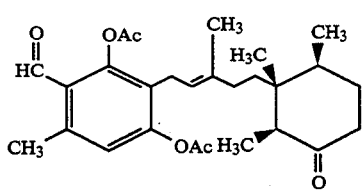

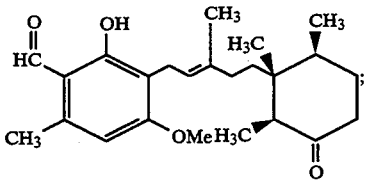

or a pharmaceutically acceptable salt thereof.

11. The method according to claim 8 wherein the compound which is administered is:

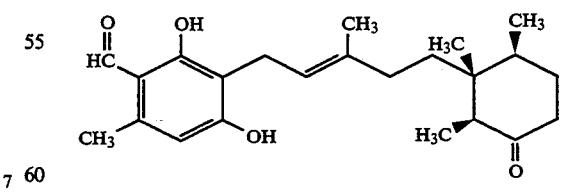

3-[5-[1(R),2(S),6(S)-trimethyl-5-oxocyclohexyl]-3-methyl-2-pentenyl]-2,4-dihydroxy-6-methylbenzaldehyde.

12. The method according to claim 8 wherein the compound which is administered is:

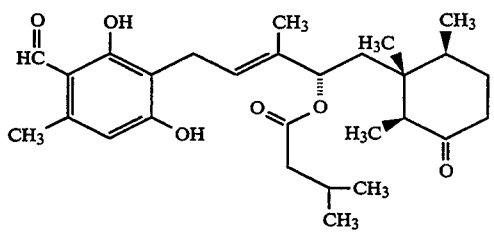

3-[5-[1(R),2(S),6(S)-trimethyl-5-oxocyclohexyl]-3-methyl-4(S)-[3-methylbutanoyloxy]-2-pentenyl]-2,4-dihydroxy-6-methylbenzaldehyde.

13. The method according to claim 8 wherein the compound which is administered is:

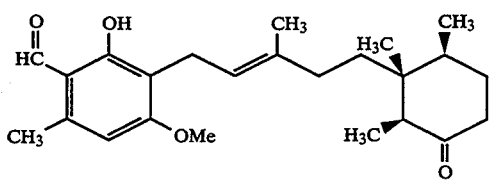

3-[5-[1(R),2(S),6(S)-trimethyl-5-oxocyclohexyl]-3-methyl-2-pentenyl]-2-hydroxy-4-methoxy-6-methylbenzaldehyde.

14. A method of treating cancer which comprises administering to a mammal in need thereof a therapeutically effective amount of a compound of the formula I:

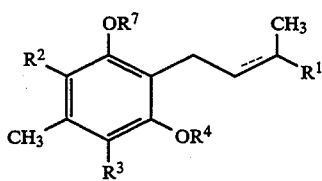

wherein:
R¹ is

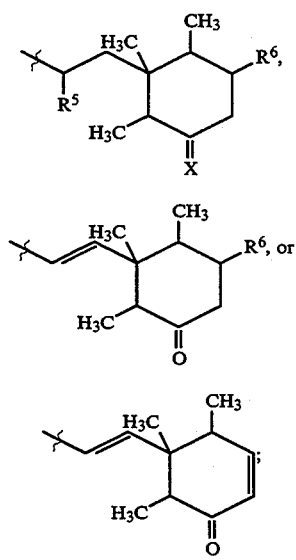

R² is hydrogen, formyl, $C_{1-4}$ alkyl, —$CO_2R^8$ or —$CH_2OH$;

$R^3$ is hydrogen or halogen;
$R^4$ is hydrogen, $C_{1-4}$ alkyl, —$CH_2OCH_3$, t-Bu(CH$_3$)$_2$Si— or acetyl;
$R^5$ is selected from:
a) hydrogen; and
b)

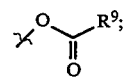

$R^6$ is hydrogen, $C_{1-4}$ alkyl or acetoxy;
$R^7$ is hydrogen, —$CH_2OCH_3$ or acyl;
$R^8$ is hydrogen or $C_1$–$C_6$ alkyl
$R^9$ is $C_1$–$C_6$ alkyl and
the dashed line represents either a bond, thereby creating a double bond, or the absence of a second bond; and
X is O or —OH, H;
or a pharmaceutically acceptable salt thereof.

15. A pharmaceutical composition comprising a pharmaceutical carrier, and dispersed therein, a therapeutically effective amount of a compound of claim 2.

16. A method for inhibiting farnesyl-protein transferase which comprises administering to a mammal in need thereof a therapeutically effective amount of a composition of claim 15.

17. A method for treating cancer which comprises administering to a mammal in need thereof a therapeutically effective amount of a composition of claim 15.

18. A culture of MF5710 (ATCC 74261), or an active mutant thereof.

19. The culture according to claim 18 capable of producing a compound having the formula I:

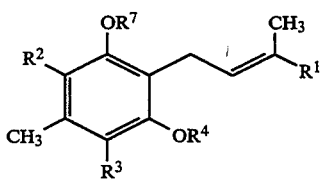

wherein:
R¹ is

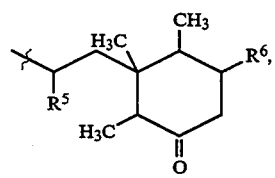

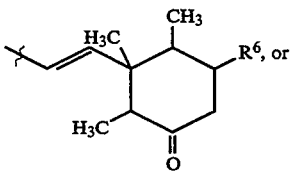

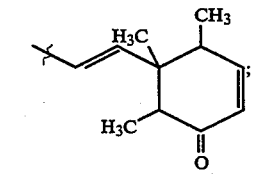

$R^2$ is hydrogen, formyl or $C_{1-4}$ alkyl;
$R^3$ is hydrogen or halogen;
$R^4$ is hydrogen;
$R^5$ is selected from:
 a) hydrogen; and
 b)

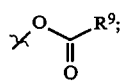

$R^6$ is hydrogen, $C_{1-4}$ alkyl or acetoxy;
$R^7$ is hydrogen or acyl;
$R^8$ is hydrogen or $C_1$–$C_6$ alkyl
$R^9$ is $C_1$–$C_6$ alkyl;
in recoverable amounts.

20. A process of preparing a compound having the formula I:

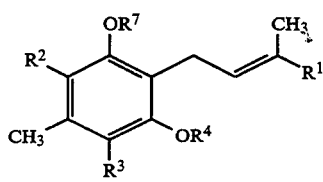

wherein:

$R^1$ is

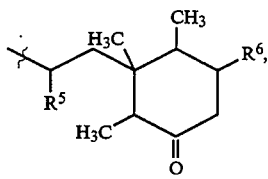

$R^2$ is hydrogen, formyl or $C_{1-4}$ alkyl;
$R^3$ is hydrogen or halogen;
$R^4$ is hydrogen;
$R^5$ is selected from:
 a) hydrogen; and
 b)

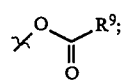

$R^6$ is hydrogen, $C_{1-4}$ alkyl or acetoxy;
$R^7$ is hydrogen or acyl;
$R^8$ is hydrogen or $C_1$–$C_6$ alkyl
$R^9$ is $C_1$–$C_6$ alkyl;
which comprises cultivating MF5710 (ATCC 74261) or an active mutant thereof, under conditions suitable for the formation of the compound of formula I and recovering the compound.

* * * * *

UNITED STATES PATENT AND TRADEMARK OFFICE
CERTIFICATE OF CORRECTION

PATENT NO. : 5,420,334
DATED : May 30, 1995
INVENTOR(S) : Sheo B. Singh, Gerald F. Bills, Russell B. Lingham, Isabel Martin, Keith C. Silverman and Jack L. Smith It is certified that error appears in the above-indentified patent and that said Letters Patent is hereby corrected as shown below:

At Column 31, in Claim 8, line 28, please delete the word famesyl and insert the word farnesyl in its place.

At Column 36, in Claim 16, line 24, please delete the word famesyl and insert the word farnesyl in its place.

UNITED STATES PATENT AND TRADEMARK OFFICE
CERTIFICATE OF CORRECTION

PATENT NO. : 5,420,334

DATED : May 30, 1995

INVENTOR(S) : Sheo B. Singh, Gerald F. Bills, Russell B. Lingham, Isabel Martin, Keith C. Silverman and Jack L. Smith It is certified that error appears in the above-indentified patent and that said Letters Patent is hereby corrected as shown below:

At Column 38, in Claim 20, at line 10, please insert the following structures in its place.

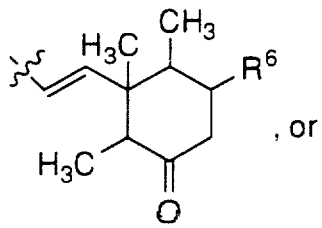 , or 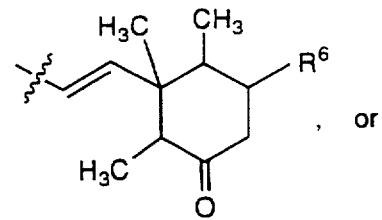 , or

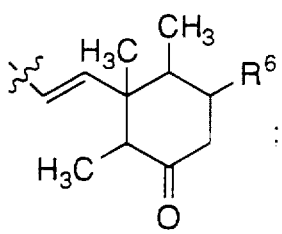 :  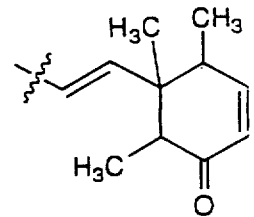

Signed and Sealed this

Third Day of October, 1995

Attest:

BRUCE LEHMAN

Attesting Officer

Commissioner of Patents and Trademarks